(12) United States Patent
Hayashi et al.

(10) Patent No.: US 8,488,867 B2
(45) Date of Patent: Jul. 16, 2013

(54) INSPECTION DEVICE FOR DISK-SHAPED SUBSTRATE

(75) Inventors: Yoshinori Hayashi, Yokohama (JP); Hiroshi Wakaba, Yokohama (JP); Yoko Ono, Yokohama (JP); Koichi Miyazono, Yokohama (JP); Hideki Mori, Yokohama (JP)

(73) Assignee: Shibaura Mechatronics Corporation, Yokohama-shi (JP)

( * ) Notice: Subject to any disclaimer, the term of this patent is extended or adjusted under 35 U.S.C. 154(b) by 455 days.

(21) Appl. No.: 12/738,760

(22) PCT Filed: Oct. 22, 2008

(86) PCT No.: PCT/JP2008/069125
§ 371 (c)(1),
(2), (4) Date: Apr. 19, 2010

(87) PCT Pub. No.: WO2009/054403
PCT Pub. Date: Apr. 30, 2009

(65) Prior Publication Data
US 2010/0246934 A1 Sep. 30, 2010

(30) Foreign Application Priority Data
Oct. 23, 2007 (JP) .................. 2007-275174
Oct. 23, 2007 (JP) .................. 2007-275175

(51) Int. Cl.
*G06K 9/00* (2006.01)

(52) U.S. Cl.
USPC .................................................. 382/144

(58) Field of Classification Search
USPC ................................. 382/144, 145
See application file for complete search history.

(56) References Cited

U.S. PATENT DOCUMENTS

| 5,258,844 A | * | 11/1993 | Nakayama et al. ........ 348/333.1 |
| 2003/0169916 A1 | | 9/2003 | Hayashi et al. ............... 382/145 |
| 2009/0177415 A1 | | 7/2009 | Hayashi et al. ................. 702/40 |

FOREIGN PATENT DOCUMENTS

| JP | 2007/-142181 | 6/2007 |
| WO | 2005/008170 | 1/2005 |
| WO | 2007/066659 | 6/2007 |

OTHER PUBLICATIONS

English translation of the essential portion of the examination report issued Sep. 24, 2012 in German counterpart application (7 pages).

* cited by examiner

*Primary Examiner* — Tarifur Chowdhury
*Assistant Examiner* — Abdullahi Nur
(74) *Attorney, Agent, or Firm* — Kratz, Quintos & Hanson, LLP

(57) ABSTRACT

An inspection apparatus to precisely quantitatively inspect positions of formation of film layers formed on the surface of a disk-shaped substrate. It generates captured image data expressing a captured image corresponding to a field of vie based on image signals successively output from an image capturing unit capturing an image of a predetermined surface at an outer circumference part of the disk-shaped substrate and generates film layer edge position information expressing longitudinal direction positions at corresponding positions along the circumferential direction of an edge line of a film layer image pan corresponding to the film layer on the surface image with reference to, from the captured image data, longitudinal direction positions at the different positions along the circumferential direction of a boundary line between a surface image part corresponding to the predetermined surface on the captured image and its outer image part.

15 Claims, 21 Drawing Sheets

$$Y_4(\theta) = Y(\theta) - Y_{E15aL}(\theta)$$

$$Y_{4E24}(\theta) = Y_{E24}(\theta) - Y_{E15aL}(\theta)$$

$$Y_1(\theta) = Y(\theta) - Y_{E15a}(\theta)$$
$$Y_{1E23}(\theta) = Y_{E23}(\theta) - Y_{E15a}(\theta)$$
$$Y_{1E15b}(\theta) = Y_{E15bL}(\theta) - Y_{E15a}(\theta)$$

$Y_2(\theta) = Y(\theta) - Y_{E15b}(\theta)$
$Y_{2E23}(\theta) = Y_{E23}(\theta) - Y_{E15b}(\theta)$
$Y_{2E22}(\theta) = Y_{E22}(\theta) - Y_{E15b}(\theta)$
$Y_{2E15c}(\theta) = Y_{E15cL}(\theta) - Y_{E15b}(\theta)$ $$Y_3(\theta) = Y(\theta) - Y_{E15c}(\theta)$$
$$Y_{3E22}(\theta) = Y_{E22}(\theta) - Y_{E15c}(\theta)$$
$$Y_{3E21}(\theta) = Y_{E21}(\theta) - Y_{E15c}(\theta)$$
$$Y_{3E15d}(\theta) = Y_{E15dL}(\theta) - Y_{E15c}(\theta)$$

$Y_5(\theta) = Y(\theta) - Y_{E15d}(\theta)$

INSPECTION DEVICE FOR DISK-SHAPED SUBSTRATE

TECHNICAL FIELD

The present invention relates to an inspection apparatus of a disk-shaped substrate which inspects outer circumference parts of semiconductor wafers and other disk-shaped substrates by images captured from the same.

BACKGROUND ART

Disk-shaped semiconductor wafers (disk-shaped substrates), for example, are structured as shown in FIG. 21A and FIG. 21B. Note that, FIG. 21A is a perspective view of a semiconductor wafer, while FIG. 21B is a cross-sectional view showing an A-A section of FIG. 21A enlarged. As shown in FIG. 21A and FIG. 21B, the semiconductor wafer 10 has an outer circumference part 10E formed by an upper outer circumference bevel surface 12U inclined from an upper surface 11a edge toward a lower surface 11b, further, a lower outer circumference bevel surface 12L conversely inclined from a lower surface 11b edge toward an upper surface 11a, and an outer circumference end face 12A connecting the upper outer circumference bevel surface 12U and lower outer circumference bevel surface 12L. Further, the outer circumference part 10E is formed with a notch 13 showing a reference position in a circumferential direction Ds.

In the process of production of such a semiconductor wafer 10, the surface is formed with a resist film, insulating film, conductive film, and various other film layers (see, for example, Patent Literature 1). These film layers are required in the process of production of the semiconductor wafer 10 or are required for exhibiting a designed function. The objectives are diverse as well. Regions for their formation are determined in accordance with the objectives. There are film layers which should be formed on the upper surface 11a so as not to reach the boundary with the upper outer circumference bevel surface 12U, film layers which should be formed from the upper surface 11a to the upper outer circumference bevel surface 12U, film layers to be formed from the upper surface 11a past the upper outer circumference bevel surface 12U up to the outer circumference end face 12A, and, furthermore, film layers which should be formed from the upper surface 11a past the upper outer circumference bevel surface 12U and outer circumference end face 12A up to the lower outer circumference bevel surface 12L, etc.

Patent Literature 1: Japanese Patent Publication (A) No. 2007-142181

DISCLOSURE OF INVENTION

Technical Problem

In view of this situation, it has become necessary to inspect which surfaces of the outer circumference part 10E of the semiconductor wafer 10 the front end edge lines of the film layers have reached, but in the past there has not been any system for quantitatively inspecting the positions of such edge lines.

Further, it is necessary to inspect the states of film layers formed on the surface of a wafer 10 (for example, peeling, positions of edge lines, etc.), but in the past there has never been an inspection apparatus able to precisely evaluate the states of film layers at a wafer 10 having film layers formed across a plurality of contiguous surfaces. Further, the conventional inspection apparatuses were not able to precisely evaluate the states of scratches formed over a plurality of contiguous surfaces or foreign matter deposited over a plurality of contiguous surfaces on the wafer 10.

The present invention was made in consideration of the above-mentioned situation and provides an inspection apparatus of a disk-shaped substrate which can quantitatively inspect the positions of formation of film layers formed on the surface of a disk-shaped substrate.

Further, the present invention provides an inspection apparatus of a disk-shaped substrate able to more precisely inspect (evaluate) the states of a plurality of contiguous surfaces of a disk-shaped substrate.

Solution to Problem

The inspection apparatus of a disk-shaped substrate according to the present invention is an inspection apparatus of a disk-shaped substrate having film layers formed on its surface, which has an image capturing unit having a capturing view field including a predetermined surface at an outer circumference part of said disk-shaped substrate, successively capturing images of said predetermined surface in a circumferential direction of said disk-shaped substrate, and outputting image signals and an image processor processing the image signals successively output from said image capturing unit; said image processor having an image data generating means for generating captured image data expressing a captured image corresponding to said capturing view field extending corresponding to the circumferential direction of said disk-shaped substrate based on said image signals and a film layer edge position information generating means for using as a reference longitudinal direction positions showing positions in a direction traversing said circumferential direction at respective positions along said circumferential direction of a boundary line between a surface image part corresponding to said predetermined surface on said captured image and its outer image part so as to generate, from said captured image data, film layer edge position information expressing longitudinal direction positions at corresponding positions along said circumferential direction of edge lines of film layer image parts corresponding to said film layers on said surface image part, said film layer edge position information being able to be used to evaluate positions of formation of said film layers at said disk-shaped substrate.

Due to such a configuration, from captured image data expressing a captured image corresponding to a field of view including a predetermined surface at an outer circumference part of a disk-shaped substrate, film layer edge position information expressing longitudinal direction positions at corresponding positions along said circumferential direction of the edge line of a film layer image part corresponding to said film layer on said surface image part is generated with reference to longitudinal direction positions showing positions in a direction traversing said circumferential direction at different positions along said circumferential direction of a boundary line between a surface image part corresponding to said predetermined surface on said captured image and its outer image part, so it becomes possible to use this film layer edge position information to express the position of an edge line of a film layer formed on a predetermined surface at an outer circumference part of a disk-shaped substrate.

Further, the inspection apparatus of a disk-shaped substrate according to the present invention can be configured so that said film layer edge position information generating means has a means for detecting longitudinal direction positions at different positions along said circumferential direction of a boundary line between said surface image part on said captured image and said outer image part, a means for detecting longitudinal direction positions at different positions along said circumferential direction of an edge line of said film layer image part on said surface image part, and a correcting means for correcting detected longitudinal direction positions at different positions along said circumferential direction of an edge line of said film layer image part so that the longitudinal direction positions at the corresponding positions along said circumferential direction of the boundary line between said surface image part and said outer image part is used as a reference, and generating said film layer edge position information.

Due to such a configuration, longitudinal direction positions at different positions along said circumferential direction of an edge line of said film layer image part on said surface image part are corrected with reference to the longitudinal direction positions at the corresponding positions along said circumferential direction of the boundary line between said surface image part and said outer image part on the captured image, so it becomes possible to obtain said film layer edge position information with reference to said boundary line.

Further, the inspection apparatus of a disk-shaped substrate according to the present invention can be configured so that said disk-shaped substrate is a semiconductor wafer formed with an upper outer circumference bevel surface inclined from its upper surface edge toward a lower surface, a lower outer circumference bevel surface inclined from said lower surface edge toward said upper surface, and an outer circumference end face connecting said upper outer circumference bevel surface and said lower outer circumference bevel surface at its outer circumference part, and said image capturing unit captures an image of either of a region of said upper surface adjoining said upper outer circumference bevel surface, said upper outer circumference bevel surface, said outer circumference end face, said lower outer circumference bevel surface, and a region of said lower surface adjoining said lower outer circumference bevel surface.

Due to such a configuration, a position of an edge line of a film layer formed on any surface at the outer circumference part of the semiconductor wafer including a region of the upper surface adjoining the upper outer circumference bevel surface, upper outer circumference bevel surface, outer circumference end face, lower outer circumference bevel surface, and region of the lower surface adjoining the lower outer circumference bevel surface can be expressed by the film layer edge position information.

Furthermore, the inspection apparatus of a disk-shaped substrate according to the present invention can be configured so that said image capturing unit captures an image of a region of said upper surface of said semiconductor wafer adjoining said upper outer circumference bevel surface, said image data generating means uses the image signals successively output from said image capturing unit as a basis to generate captured image data expressing a captured image corresponding to a field of view including the region of said upper surface adjoining said upper outer circumference bevel surface extending along the circumferential direction of said semiconductor wafer, and said film layer edge position information generating means uses as a reference, from said captured image data, longitudinal direction positions at positions along said circumferential direction of a boundary line between an upper surface image part corresponding to the region of said upper surface adjoining said upper outer circumference bevel surface on said captured image and an outer image part at the upper outer circumference bevel surface side so as to generate film layer edge position information expressing longitudinal direction positions at corresponding positions along said circumferential direction of an edge line of a film layer image part corresponding to said film layer at said upper surface image part.

Due to such a configuration, the position of an edge line of a film layer formed at a region of the upper surface of the outer circumference part of the semiconductor wafer adjoining the upper outer circumference bevel surface can be expressed by the film layer edge position information.

Further, the inspection apparatus of a disk-shaped substrate according to the present invention can be configured so that said image capturing unit captures an image of said upper outer circumference bevel surface of said semiconductor wafer, said image data generating means uses the image signals successively output from said image capturing unit as a basis to generate captured image data expressing a captured image corresponding a field of view including said upper outer circumference bevel surface extending corresponding to the circumferential direction of said semiconductor wafer, and said film layer edge position information generating means uses as a reference, from said captured image data, longitudinal direction positions at different positions along said circumferential direction of a boundary line between an upper outer circumference bevel surface image part corresponding to said upper outer circumference bevel surface on said captured image and either an outer image part at the upper surface side or outer image part of the outer circumference end face side so to generate film layer edge position information expressing longitudinal directional positions at corresponding positions along said circumferential direction of an edge line of a film layer image part corresponding to said film layer at said upper outer circumference bevel surface image part.

Due to such a configuration, positions of the edge line of a film layer formed on the upper outer circumference bevel surface at the outer circumference part of the semiconductor wafer can be expressed by the film layer edge position information.

Further, the inspection apparatus of a disk-shaped substrate according to the present invention can be configured so that said image capturing unit captures an image of said outer circumference end face of said semiconductor wafer, said image data generating means uses the image signals successively output from said image capturing unit as a basis to generate captured image data expressing a captured image corresponding a field of view including said outer circumference end face extending corresponding to the circumferential direction of said semiconductor wafer, and said film layer edge position information generating means uses as a reference, from said captured image data, longitudinal direction positions at different positions along said circumferential direction of a boundary line between an outer circumference bevel end face image part corresponding to said outer circumference end face on said captured image and either an outer image part at the upper outer circumference bevel surface side or outer image part of the lower outer circumference bevel surface side so as to generate film layer edge position information expressing longitudinal directional positions at corresponding positions along said circumferential direction of an edge line of a film layer image part corresponding to said film layer at said upper outer circumference end face image part.

Due to such a configuration, the positions of the edge line of a film layer formed at an outer circumference end face of the outer circumference part of a semiconductor wafer can be expressed by the film layer edge position information.

Furthermore, the inspection apparatus of a disk-shaped substrate according to the present invention can be configured so that said image capturing unit captures an image of said lower outer circumference bevel surface of said semiconductor wafer, said image data generating means uses the image signals successively output from said image capturing unit as a basis to generate captured image data expressing a captured image corresponding to a field of view including said lower outer circumference bevel surface extending corresponding to the circumferential direction of said semiconductor wafer, and said film layer edge position information generating means uses longitudinal direction positions at different positions along said circumferential direction of a boundary line between a lower outer circumference bevel surface image part corresponding to said lower outer circumference bevel surface on said captured image and either of an outer image part at the outer circumference end face side and outer image part at the lower surface side as a reference and generates, from said captured image data, film layer edge position information expressing longitudinal direction positions at corresponding positions along said circumferential direction of an edge line of the film layer part corresponding to said film layer on said lower outer circumference bevel surface image.

Due to such a configuration, the positions of the edge line of a film layer formed on the lower outer circumference bevel surface at the outer circumference part of the semiconductor wafer can be expressed by the film layer edge position information.

Further, the inspection apparatus of a disk-shaped substrate according to the present invention can be configured so that said image capturing unit captures an image of a region of said lower surface of said semiconductor wafer adjoining said lower outer circumference bevel surface, said image data generating means uses the image signals successively output from said image capturing unit as a basis to generate captured image data expressing a captured image corresponding to a field of view including a region of said lower surface of said semiconductor wafer adjoining said lower outer circumference bevel surface extending corresponding to the circumferential direction, and said film layer edge position information generating means uses as a reference, from said captured image data, longitudinal direction positions at different positions along said circumferential direction of a boundary line between a bottom surface image part corresponding to a region of said lower surface on said captured image adjoining said lower outer circumference bevel surface and an outer image part at the lower outer circumference bevel surface side so as to generate film layer edge position information expressing longitudinal direction positions at corresponding positions along said circumferential direction of an edge line of a film layer image part corresponding to said film layer at said bottom surface image part.

Due to such a configuration, the positions of the edge line of a film layer formed at a region of the lower surface of the outer circumference part of the semiconductor wafer adjoining the lower outer circumference bevel surface can be expressed by the film layer edge position information.

The inspection apparatus of a disk-shaped substrate according to the present invention is an inspection apparatus of a disk-shaped substrate having film layers formed on its surface, which has an image capturing unit having individual capturing view fields each of which includes one of a plurality of surfaces continuous along a direction traversing a circumferential direction at the outer circumference part of said disk-shaped substrate, successively capturing images of said plurality of surfaces in the circumferential direction of said disk-shaped substrate, and outputting image signals and an image processor processing the image signals successively output from said image capturing unit; said image processor having an image data generating means for generating captured image data expressing a captured image corresponding to each of said capturing view fields respectively including said plurality of surfaces extending corresponding to the circumferential direction of said disk-shaped substrate based on said image signals, a correcting means for correcting said captured image data expressing the captured image so that longitudinal direction positions at corresponding positions along said circumferential direction of respective pixel points are expressed with reference to longitudinal direction positions showing positions in a direction traversing said circumferential direction at respective positions along said circumferential direction of a boundary line between a surface image part corresponding to the surface on said captured image corresponding to each of the capturing view fields respectively including said plurality of surfaces and an outer image part at one side adjoining said surface, an image combining means for using said corrected captured image data expressing the captured image corresponding to each of the capturing view fields respectively including said plurality of surfaces, and generating image data expressing a composite image in which said plurality of surface image parts corresponding to said plurality of surfaces are combined so that their corresponding boundary lines are matched, in which composite image longitudinal direction positions at corresponding positions along said circumferential direction of the respective pixel points are determined with reference to longitudinal direction positions at respective positions along said circumferential direction of a reference boundary line, the boundary line on the captured image corresponding to a capturing view field including a predetermined surface of said plurality of surfaces being used as the reference boundary line, and a film layer edge position information generating means for generating film layer edge position information showing longitudinal direction positions at different positions along said circumferential direction of edge lines of film layer image parts corresponding to said film layers on said composite image, said film layer edge position information being able to be used to evaluate positions of formation of said film layers at said disk-shaped substrate.

Due to such a configuration, captured image data is generated expressing captured images so that longitudinal direction positions at corresponding positions along said circumferential direction of the different pixel points of said captured images are expressed with reference to longitudinal direction positions at different positions along said circumferential direction of boundary lines between surface images corresponding to surfaces on captured images corresponding to fields of view including the plurality of surfaces and outer image parts of first sides adjoining said surfaces. From such captured image data, composite image data is generated expressing a composite image of the surface image parts corresponding to said plurality of surfaces combined so that their corresponding boundary lines match, wherein a boundary line on a captured image corresponding to a field of view including a predetermined surface among said plurality of surfaces is used as a reference boundary line and wherein longitudinal direction positions at corresponding positions along said circumferential direction of the different pixel points are determined with reference to longitudinal direction positions at different positions along said circumferential direction of the reference boundary line. Also film layer edge position information is generated showing longitudinal direction positions at corresponding positions along said circumferential direction of edge lines of film layer image parts corresponding to said film layers on said composite image. This film layer edge position information may be used to uniformly express positions of the edge line for a film layer formed at any of the plurality of surfaces of the outer circumference part of a disk-shaped substrate.

Further, the inspection apparatus of a disk-shaped substrate according to the present invention can be configured so that said disk-shaped substrate is a semiconductor wafer on which an upper outer circumference bevel surface inclined from an edge of an upper surface toward a lower surface, an outer circumference end face contiguous from the edge of said upper outer circumference bevel surface, and a lower outer circumference bevel surface inclined from the lower surface toward said upper surface and contiguous from said outer circumference end face are formed contiguously in a direction traversing said circumferential direction, and said plurality of surfaces are two or more contiguous surfaces among a region of said upper surface adjoining said upper outer circumference bevel surface, said upper outer circumference bevel surface, outer circumference end face, lower outer circumference bevel surface, and a region of the lower surface adjoining said lower outer circumference bevel surface.

Due to such a configuration, even at film layers formed at any two or more contiguous surfaces of the outer circumference part of the semiconductor wafer including a region of the upper surface adjoining the upper outer circumference bevel surface, the upper outer circumference bevel surface, the outer circumference end face, the lower outer circumference bevel surface, and the region of the lower surface adjoining the lower outer circumference bevel surface, positions of the edge line can be expressed uniformly by film layer edge position information.

Furthermore, the inspection apparatus of a disk-shaped substrate according to the present invention can be configured so that said plurality of surfaces are said upper outer circumference bevel surface, outer circumference end face, and lower outer circumference bevel surface; said image data generating means uses the image signals successively output from said image capturing unit as a basis to generate first captured image data expressing a first captured image corresponding to a field of view including said upper outer circumference bevel surface extending corresponding to the circumferential direction of said semiconductor wafer, second captured image data expressing a second captured image corresponding to a field of view including said outer circumference end face, and third captured image data expressing a third captured image corresponding to a field of view including said lower outer circumference bevel surface; said correcting means corrects said first captured image data so that longitudinal direction positions at corresponding positions along said circumferential direction of different pixel points on said first captured image are expressed with reference to longitudinal direction positions at different positions along said circumferential direction of a boundary line of an upper outer circumference bevel surface image part corresponding to said upper outer circumference bevel surface on said first captured image and an outer image part at an upper surface side of the same, corrects said second captured image data so that longitudinal direction positions at corresponding positions along said circumferential direction of different pixel points on said second captured image are expressed with reference to longitudinal direction positions at different positions along said circumferential direction of a boundary line between an outer circumference end face image part corresponding to said outer circumference end face on said second captured image and an outer image part at an upper outer circumference bevel surface side of the same, and corrects said third captured image data so that longitudinal direction positions at corresponding positions along said circumferential direction of different pixel points on said third captured image are expressed with reference to longitudinal direction positions at different positions along said circumferential direction of a boundary line between a lower outer circumference bevel image part corresponding to said lower outer circumference bevel surface on said third captured image and an outer image part at the outer circumference end face side of the same; and said image combining means uses the corrected first captured image data, second captured image data, and third captured image data to generate composite image data showing a composite image of said upper outer circumference bevel surface image part, said outer circumference end face image part, and said lower outer circumference bevel surface image part combined so that their corresponding boundary lines match, wherein said boundary line on said first captured image is used as a reference boundary line and wherein longitudinal direction positions at corresponding positions along said circumferential direction of the different pixel points are determined with reference to longitudinal direction positions at different positions along said circumferential direction of said reference boundary line.

Due to such a configuration, even at a film layer formed at any of the surfaces contiguous at the outer circumference part of the semiconductor wafer in a direction traversing the circumferential direction such as the upper outer circumference bevel surface, the outer circumference end face, and the lower outer circumference bevel surface, positions of the edge line can be expressed uniformly by the film layer edge position information.

Further, the inspection apparatus of a disk-shaped substrate according to the present invention can be configured so that said plurality of surfaces are a region of the upper surface of said semiconductor wafer adjoining said upper outer circumference bevel surface, said upper outer circumference bevel surface, outer circumference end face, lower outer circumference bevel surface, and region of the lower surface of said semiconductor wafer adjoining said lower outer circumference bevel surface; said image data generating means uses the image signals successively output from said image capturing unit as a basis to generate first captured image data expressing a first captured image corresponding to a field of view including said upper outer circumference bevel surface extending corresponding to the circumferential direction of said semiconductor wafer, second captured image data expressing a second captured image corresponding to a field of view including said outer circumference end face, third captured image data expressing a third captured image corresponding to a field of view including said lower outer circumference bevel surface, fourth captured image data expressing a fourth captured image corresponding to a field of view including a region of said upper surface adjoining the upper outer circumference bevel surface, and fifth captured image data expressing a fifth captured image corresponding to a field of view including a region of said lower surface adjoining said lower outer circumference bevel surface; said correcting means corrects said first captured image data so that longitudinal direction positions at corresponding positions along said circumferential direction of different pixel points on said first captured image are expressed with reference to longitudinal direction positions at different positions along said circumferential direction of a boundary line of an upper outer circumference bevel surface image part corresponding to said upper outer circumference bevel surface on said first captured image and an outer image part at an upper surface side of the same, corrects said second captured image data so that longitudinal direction positions at corresponding positions along said circumferential direction of different pixel points on said second captured image are expressed with reference to longitudinal direction positions at different positions along said circumferential direction of a boundary line between an outer circumference end face image part corresponding to said outer circumference end face on said second captured image and an outer image part at an upper outer circumference bevel surface side of the same, corrects said third captured image data so that longitudinal direction positions at corresponding positions along said circumferential direction of different pixel points on said third captured image are expressed with reference to longitudinal direction positions at different positions along said circumferential direction of a boundary line between a lower outer circumference bevel image part corresponding to said lower outer circumference bevel surface on said third captured image and an outer image part at the outer circumference end face side of the same, corrects said fourth captured image data so that longitudinal direction positions at corresponding positions along said circumferential direction of different pixel points on said fourth captured image are expressed with reference to longitudinal direction positions at different positions along said circumferential direction of a boundary line between an upper surface image part corresponding to a region of said upper surface on said fourth captured image adjoining said upper outer circumference bevel surface and an outer image part at an upper outer circumference bevel surface side of the same, and corrects said fifth captured image data so that longitudinal direction positions at corresponding positions along said circumferential direction of different pixel points on said fifth captured image are expressed with reference to longitudinal direction positions at different positions along said circumferential direction of a boundary line between a bottom surface image part corresponding to a region of said lower surface on said fifth captured image adjoining said lower outer circumference bevel surface and the outer image part at the lower outer circumference bevel surface side of the same; and said image combining means uses the corrected first captured image data, second captured image data, third captured image data, fourth captured image data, and fifth captured image data to generate composite image data showing a composite image of said upper surface image part, said upper outer circumference bevel surface image part, said outer circumference end face image part, said lower outer circumference bevel surface image part, and said bottom surface image part combined so that their corresponding boundary lines match, wherein said boundary line on said first captured image is used as a reference boundary line and wherein longitudinal direction positions at corresponding positions along said circumferential direction of the different pixel points are determined with reference to longitudinal direction positions at different positions along said circumferential direction of said reference boundary line.

Due to such a configuration, even at a film layer formed at any of the surfaces of the outer circumference part of the semiconductor wafer contiguous in a direction traversing the circumferential direction such as the region of the upper surface adjoining the upper outer circumference bevel surface, the upper outer circumference bevel surface, the outer circumference end face, the lower outer circumference bevel surface, and the region of the lower surface adjoining the lower outer circumference bevel surface, positions of the edge line can be expressed uniformly by the film layer edge position information.

Further, the inspection apparatus of a disk-shaped substrate according to the present invention has an image capturing unit having individual capturing view fields each of which includes one of a plurality of surfaces contiguous along a direction traversing a circumferential direction at the outer circumference part of said disk-shaped substrate, successively capturing images of said plurality of surfaces in a circumferential direction of said disk-shaped substrate, and outputting image signals and an image processor processing the image signals successively output from said image capturing unit; said image processor having an image data generating means for generating captured image data expressing a captured image corresponding to each of said capturing view field respectively including said plurality of surfaces extending corresponding to the circumferential direction of said disk-shaped substrate based on said image signals, an image combining means for using said captured image data expressing the captured image corresponding to each of the capturing view fields respectively including said plurality of surfaces to generate composite image data expressing a composite image of the plurality of surface image parts corresponding to said plurality of surfaces combined so that their corresponding boundary lines match, and an output control means for displaying said composite image on a display unit based on said composite image data.

Due to such a configuration, using captured image data expressing captured images corresponding to fields of view including a plurality of surfaces, composite image data expressing a composite image of a plurality of surface image parts corresponding to the plurality of surfaces combined so that corresponding boundary lines match is generated and that composite image data is used as a basis to display said composite image on a display unit, so it becomes possible to comprehensively grasp the states of a plurality of contiguous surfaces of a disk-shaped substrate from the composite image displayed on the display unit.

Further, the inspection apparatus of a disk-shaped substrate according to the present invention can be configured so that said image combining means has a correcting means correcting said captured image data expressing the captured image so that longitudinal direction positions at corresponding positions along said circumferential direction of respective pixel points are expressed with reference to longitudinal direction positions expressing positions along a direction traversing said circumferential direction at respective positions along said circumferential direction of a boundary line between a surface image part corresponding to the surface on said captured image corresponding to each of the capturing view fields including said plurality of surfaces and the an outer image part at one side adjoining said surface and a composite image data generating means using said corrected captured image data expressing the captured image corresponding to each of the capturing view fields respectively including said plurality of surfaces, and generating imaged data expressing a composite image in which longitudinal direction positions at corresponding positions along said circumferential direction of the respective pixel points are determined with reference to longitudinal direction positions at respective positions along said circumferential direction of a reference boundary line, the boundary line on the captured image corresponding to a capturing view field including a predetermined surface of said plurality of surfaces being used as the reference boundary line.

Due to such a configuration, a composite image is displayed with positions of pixel points expressed with reference to a boundary line between a surface image corresponding to a predetermined surface among said plurality of surfaces on a captured image corresponding to a field of view including that predetermined surface and an outer image part at one surface adjoining it as a reference boundary line, so said composite image is displayed in accordance with a standardized reference, and it becomes possible to obtain a more precise comprehensive grasp of the states of a plurality of contiguous surfaces of a disk-shaped substrate.

Further, the inspection apparatus of a disk-shaped substrate according to the present invention can be configured so that said disk-shaped substrate is a semiconductor wafer formed with an upper outer circumference bevel surface inclined from its upper surface edge toward a lower surface, an outer circumference end face contiguous from the edge of said upper outer circumference bevel surface, and a lower outer circumference bevel surface inclined from the lower surface edge toward said upper surface and contiguous from said outer circumference end face so as to be contiguous in a direction traversing said circumferential direction, said plurality of surfaces being two or more contiguous surfaces among a region of said upper surface adjoining said upper outer circumference bevel surface, said upper outer circumference bevel surface, outer circumference end face, lower outer circumference bevel surface, and a region of said lower surface adjoining said lower outer circumference bevel surface.

Due to such a configuration, the states of any two or more contiguous surfaces on the outer circumference part of the semiconductor wafer such as the part of the upper surface adjoining the upper outer circumference bevel surface, the upper outer circumference bevel surface, the outer circumference end face, the lower outer circumference bevel surface, and the part of the lower surface adjoining the lower outer circumference bevel surface can be comprehensively grasped from the composite image.

Furthermore, the inspection apparatus of a disk-shaped substrate according to the present invention can be configured so that said plurality of surfaces are said upper outer circumference bevel surface, outer circumference end face, and lower outer circumference bevel surface; said image data generating means uses the image signals successively output from said image capturing unit as a basis to generate first captured image data expressing a first captured image corresponding to a field of view including said upper outer circumference bevel surface extending corresponding to the circumferential direction of said semiconductor wafer, second captured image data expressing a second captured image corresponding to a field of view including said outer circumference end face, and third captured image data expressing a third captured image corresponding to a field of view including said lower outer circumference bevel surface; said correcting means corrects said first captured image data so that longitudinal direction positions at corresponding positions along said circumferential direction of different pixel points on said first captured image are expressed with reference to longitudinal direction positions at different positions along said circumferential direction of a boundary line between an upper outer circumference bevel surface image part corresponding to said upper outer circumference bevel surface on said first captured image and an outer image part at an upper surface side of the same, corrects said second captured image data so that longitudinal direction positions at corresponding positions along said circumferential direction of different pixel points on said second captured image are expressed with reference to longitudinal direction positions at different positions along said circumferential direction of a boundary line between an outer circumference end face image part corresponding to said outer circumference end face on said second captured image and an outer image part at an outer circumference bevel surface side of the same, and corrects said third captured image data so that longitudinal direction positions at corresponding positions along said circumferential direction of different pixel points on said third captured image are expressed with reference to longitudinal direction positions at different positions along said circumferential direction of a boundary line between a lower outer circumference bevel image part corresponding to said lower outer circumference bevel surface on said third captured image and an outer image part at an outer circumference end face side of the same so as to; and said composite image data generating means uses the corrected first captured image data, second captured image data, and third captured image data to generate composite image data expressing a composite image of said upper outer circumference bevel surface image part, said outer circumference end face image part, and said lower outer circumference bevel surface image part combined so that their corresponding boundary lines match, wherein said boundary line on said first captured image is used as a reference boundary line and wherein the longitudinal direction position at corresponding positions along said circumference direction of the different pixel points are determined with reference to the longitudinal direction positions at different positions along said circumferential direction of said reference boundary line.

Due to such a configuration, it becomes possible to comprehensively obtain a grasp of the states of any of the surfaces at the outer circumference part of the semiconductor wafer contiguous in a direction traversing the circumferential direction such as the upper outer circumference bevel surface, outer circumference end face, and lower outer circumference bevel surface from a composite image of the same.

Further, the inspection apparatus of a disk-shaped substrate according to the present invention can be configured so that said plurality of surfaces are a region of the upper surface of said semiconductor wafer adjoining said upper outer circumference bevel surface, said upper outer circumference bevel surface, outer circumference end face, lower outer circumference bevel surface, and a region of the lower surface of said semiconductor wafer adjoining said lower outer circumference bevel surface; said image data generating means uses the image signals successively output from said image capturing unit as a basis to generate first captured image data expressing a first captured image corresponding to a field of view including said upper outer circumference bevel surface extending corresponding to the circumferential direction of said semiconductor wafer, second captured image data expressing a second captured image corresponding to a field of view including said outer circumference end face, third captured image data expressing a third captured image corresponding to a field of view including said lower outer circumference bevel surface, fourth captured image data expressing a fourth captured image corresponding to a field of view including a region of said upper surface adjoining the upper outer circumference bevel surface, and fifth captured image data expressing a fifth captured image corresponding to a field of view including a region of said lower surface adjoining said lower outer circumference bevel surface; said correcting means corrects said first captured image data so that longitudinal direction positions at corresponding positions along said circumferential direction of different pixel points on said first captured image are expressed with reference to longitudinal direction positions at different positions along said circumferential direction of a boundary line of an upper outer circumference bevel surface image part corresponding to said upper outer circumference bevel surface on said first captured image and an outer image part at an upper surface side of the same, corrects said second captured image data so that longitudinal direction positions at corresponding positions along said circumferential direction of different pixel points on said second captured image are expressed with reference to longitudinal direction positions at different positions along said circumferential direction of a boundary line between an outer circumference end face image part corresponding to said outer circumference end face on said second captured image and an outer image part at an upper outer circumference bevel surface side of the same, corrects said third captured image data so that longitudinal direction positions at corresponding positions along said circumferential direction of different pixel points on said third captured image are expressed with reference to longitudinal direction positions at different positions along said circumferential direction of a boundary line between a lower outer circumference bevel image part corresponding to said lower outer circumference bevel surface on said third captured image and an outer image part at the outer circumference end face side of the same, corrects said fourth captured image data so that longitudinal direction positions at corresponding positions along said circumferential direction of different pixel points on said fourth captured image are expressed with reference to longitudinal direction positions at different positions along said circumferential direction of a boundary line between an upper surface image part corresponding to a region of said upper surface on said fourth captured image adjoining said upper outer circumference bevel surface and an outer image part at an upper outer circumference bevel surface side of the same, and corrects said fifth captured image data so that longitudinal direction positions at corresponding positions along said circumferential direction of different pixel points on said fifth captured image are expressed with reference to longitudinal direction positions at different positions along said circumferential direction of a boundary line between a bottom surface image part corresponding to a region of said lower surface on said fifth captured image adjoining said lower outer circumference bevel surface and the outer image part at the lower outer circumference bevel surface side of the same; and said image combining means uses the corrected first captured image data, second captured image data, third captured image data, fourth captured image data, and fifth captured image data to generate composite image data showing a composite image of said upper surface image part, said upper outer circumference bevel surface image part, said outer circumference end face image part, said lower outer circumference bevel surface image part, and said bottom surface image part combined so that their corresponding boundary lines match, wherein said boundary line on said first captured image is used as a reference boundary line and wherein longitudinal direction positions at corresponding positions along said circumferential direction of the pixel points are determined with reference to longitudinal direction positions at different positions along said circumferential direction of said reference boundary line.

Due to such a configuration, the state of any surface at the outer circumference part of the semiconductor wafer contiguous along the direction traversing the circumferential direction, that is, the part of the upper surface adjoining the upper outer circumference bevel surface, the upper outer circumference bevel surface, the outer circumference end face, the lower outer circumference bevel surface, and the part of the lower surface adjoining the lower outer circumference bevel surface, can also be comprehensively grasped from the composite image.

Advantageous Effects of Invention

According to the present invention, from captured image data expressing a captured image corresponding to a field of view including a predetermined surface at an outer circumference part of a disk-shaped substrate, film layer edge position information expressing longitudinal direction positions at corresponding positions along said circumferential direction of edge lines of film layer image parts corresponding to said film layers on said surface image is generated with reference to longitudinal direction positions expressing positions along a direction traversing said circumferential direction at different positions along the circumferential direction of said disk-shaped substrate of a boundary line between a surface image part corresponding to said predetermined surface on said captured image and its outer image part. This film layer edge position information can be used to express the positions of an edge line of a film layer formed on a predetermined surface at an outer circumference part of the disk-shaped substrate, so it becomes possible to quantitatively inspect positions of formation of film layers formed on the surface of the disk-shaped substrate.

Further, according to the present invention, from captured image data expressing captured images corresponding to fields of view including a plurality of contiguous surfaces, composite image data expressing a composite image of a plurality of surface image parts corresponding to the plurality of surfaces combined so that the corresponding boundary lines match is obtained. Based on this, a composite image is displayed on a display unit. From that, it becomes possible to comprehensively grasp the states of a plurality of contiguous surfaces of a disk-shaped substrate, so it becomes possible to more precisely inspect (evaluate) the states of a plurality of contiguous surfaces of the disk-shaped substrate.

BRIEF DESCRIPTION OF DRAWINGS

FIG. 15B A view showing corrected positions $Y_4$ on an image correcting the positions Y at FIG. 15A with reference to boundary line positions $Y_{E15a(\theta)}$ corresponding to the first boundary edge 15a.

FIG. 16B A view showing positions $Y_1$ on an image correcting the positions Y at FIG. 16A with reference to boundary line positions $Y_{E15a(\theta)}$ corresponding to the first boundary edge 15a.

Figure 1:
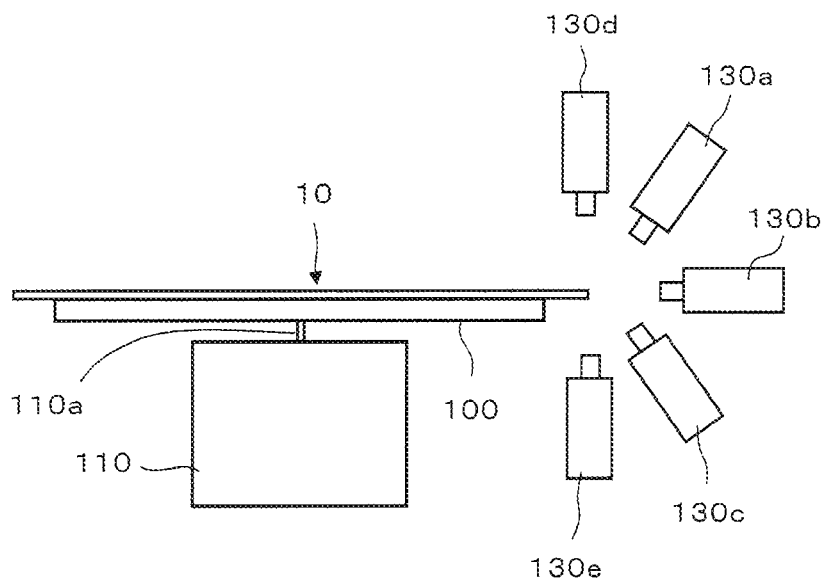
FIG. 1 A view schematically showing main parts of an image capturing apparatus of an edge inspection apparatus of a semiconductor wafer as an inspection apparatus of a disk-shaped substrate according to an embodiment of the present invention.

REFERENCE SIGNS LIST 10 semiconductor wafer
10E outer circumference part
11a upper surface
11b lower surface
12U upper outer circumference bevel surface
12A outer circumference end face
12L lower outer circumference bevel surface
15a first boundary edge
15b second boundary edge
15c third boundary edge
15d fourth boundary edge
20 film layer
21 first film layer
22 second film layer
23 third film layer
24 fourth film layer
100 stage
110 rotational drive motor
130a first camera unit
130b second camera unit
130c third camera unit
130d fourth camera unit
130e fifth camera unit
200 processing unit
210 operating unit
220 display unit

BEST MODE FOR CARRYING OUT INVENTION

Below, embodiments of the present invention will be explained using the drawings.

An inspection apparatus of a disk-shaped substrate according to an embodiment of the present invention is, for example, realized by an edge inspection apparatus of a semiconductor wafer. The image capturing system of this edge inspection apparatus of a semiconductor wafer is, for example, configured as shown in FIG. 1.

In FIG. 1, a stage 100 is held on a shaft 110a of a rotational drive motor 110 and designed to be able to be rotated in a certain direction. On the stage 10, a semiconductor wafer for forming a disk-shaped substrate (below, referred to simply as a "wafer") 10 is set in a horizontal state. Note that, the stage 100 is provided with an alignment mechanism (not shown). The position of the wafer 10 on the stage 100 is designed to be adjusted so that the center of the wafer 10 matches with the center of rotation of the stage 100 (axial center of shaft 110a) as much as possible.

Facing the outer circumference part of the wafer 10 set on the stage 100, a first camera unit 130a, a second camera unit 130b, a third camera unit 130c, a fourth camera unit 130d, and a fifth camera unit 130e, that is, five camera units (for example, cameras housing CCD line sensors as image capturing devices) are arranged. These five camera units 130a to 130e constitute the image capturing unit in the edge inspection apparatus.

Figure 21A:
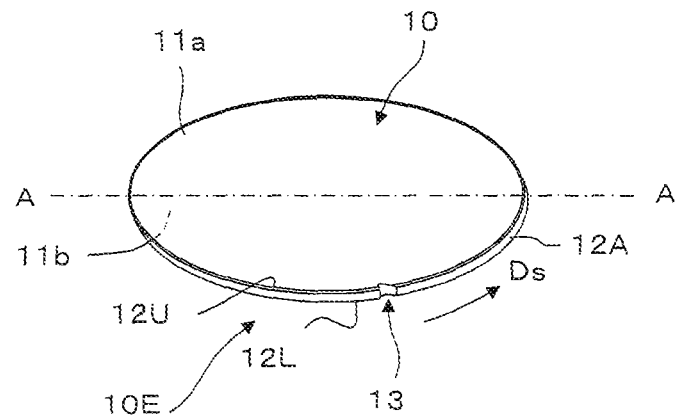
FIG. 21A A perspective view showing the appearance of a semiconductor wafer.
Figure 21B:
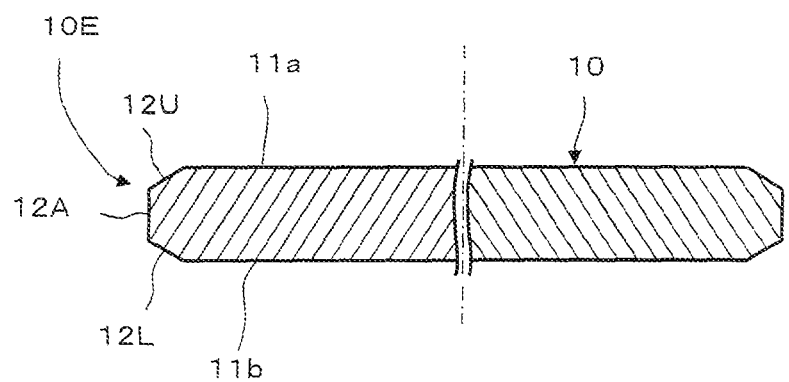
FIG. 21B A cross-sectional view showing a section A-A at FIG. 21A enlarged.

At an outer circumference part 10E of the wafer 10, as explained referring to FIG. 21, an upper outer circumference bevel surface 12U contiguous from an upper surface 11a, an outer circumference end face 12A, and a lower outer circumference bevel surface 12L contiguous at the lower surface 11b are formed contiguous in a direction traversing the circumferential direction Ds. The specific layout of the five camera units 130a, 130b, 130c, 130d, and 130e with respect to the wafer 10 is as shown in FIG. 2.

Figure 2:
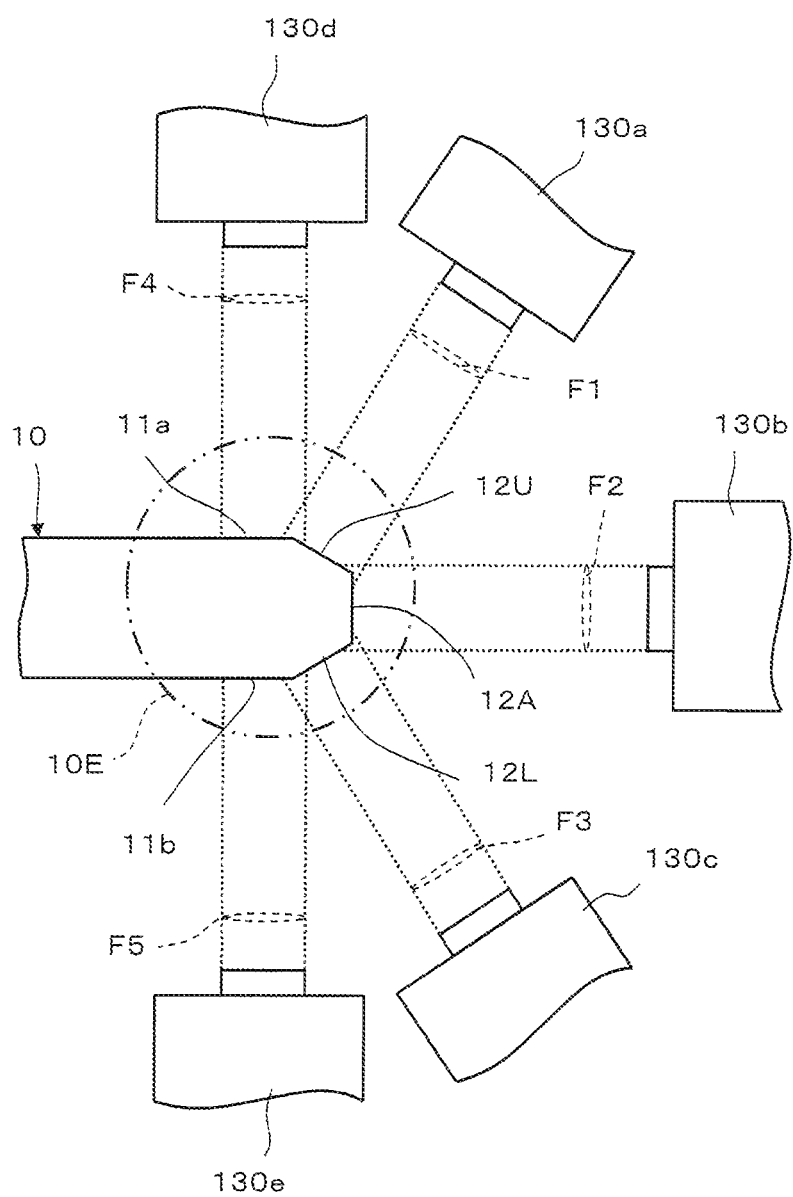
FIG. 2 A view showing field of views of five camera units for capturing the outer circumference part of a semiconductor wafer.

In FIG. 2, the first camera unit 130a is arranged to frontally face the upper outer circumference bevel surface 12U. Its field of view F1 includes the upper outer circumference bevel surface 12U and spreads slightly to the upper surface 11a side and outer circumference end face 12A side. The second camera unit 130b is arranged to frontally face the outer circumference end face 12A. Its field of view F2 includes the outer circumference end face 12A and spreads slightly to the upper outer circumference bevel surface 12U side and lower outer circumference bevel surface 12L side. The third camera unit 130c is arranged to frontally face the lower outer circumference bevel surface 12L. Its field of view F3 includes the lower outer circumference bevel surface 12L and spreads slightly to the outer circumference end face 12A side and lower surface 11b side. The fourth camera unit 130d is arranged to frontally face the region of the upper surface 11a adjoining the upper outer circumference bevel surface 12U (below, suitably referred to as the "upper surface outer circumference part"). Its field of view F4 includes the upper surface outer circumference part and spreads slightly to the upper outer circumference bevel surface 12U side. Further, the fifth camera unit 130e is arranged to frontally face the region of the lower surface 11b adjoining the lower outer circumference bevel surface 12L (below, suitably referred to as the "lower surface outer circumference part"). Its field of view F5 includes the lower surface outer circumference part and spreads slightly to the lower outer circumference bevel surface 12L side.

Note that, FIG. 2 does not show an illumination system, but in actuality, illumination light is fired at the surfaces 11a, 12U, 12A, 12L, and 11b of the outer circumference part 10E of the wafer 10 so that the light reflected from the surfaces effectively strikes the corresponding facing five camera units 130a, 130b, 130c, 130d, and 130e. Further, the depths of field of the camera units 130a, 130b, 130c, 130d, and 130e are, for example, set so that the surfaces which the camera units frontally face are reliably caught.

Further, the CCD line sensors used as image capturing devices of the camera units 130a, 130b, 130c, 130d, and 130e are arranged so as to extend in a direction substantially perpendicularly traversing the circumferential direction of the wafer 10 (Ds: direction perpendicular to paper surface of FIG. 2).

In the edge inspection apparatus of a wafer 10 having the above-mentioned image capturing system, in the process of the wafer 10 rotating along with rotation of the stage, the first camera unit 130a scans the upper outer circumference bevel surface 12, the second camera unit 130b scans the outer circumference end face 12A, the third camera unit 130c scans the lower outer circumference bevel surface 12L, the fourth camera unit 130d scans the upper surface outer circumference part, and the fifth camera unit 130e scans the lower surface outer circumference part for a successive scan (sub scan) in the circumferential direction (Ds). Due to this, the first camera unit 130a captures an image of the upper outer circumference bevel surface 12U in the circumferential direction Ds to successively output pixel units of image signals, the second camera unit 130b captures an image of the outer circumference end face 12A in the circumferential direction Ds to successively output pixel units of image signals, the third camera unit 130c captures an image of the lower outer circumference bevel surface 12U in the circumferential direction Ds to successively output pixel units of image signals, the fourth camera unit 130d captures an image of the upper surface outer circumference part in the circumferential direction Ds to successively output pixel units of image signals, and the fifth camera unit 130e captures an image of the lower surface outer circumference part in the circumferential direction Ds to successively output pixel units of image signals.

Figure 3:
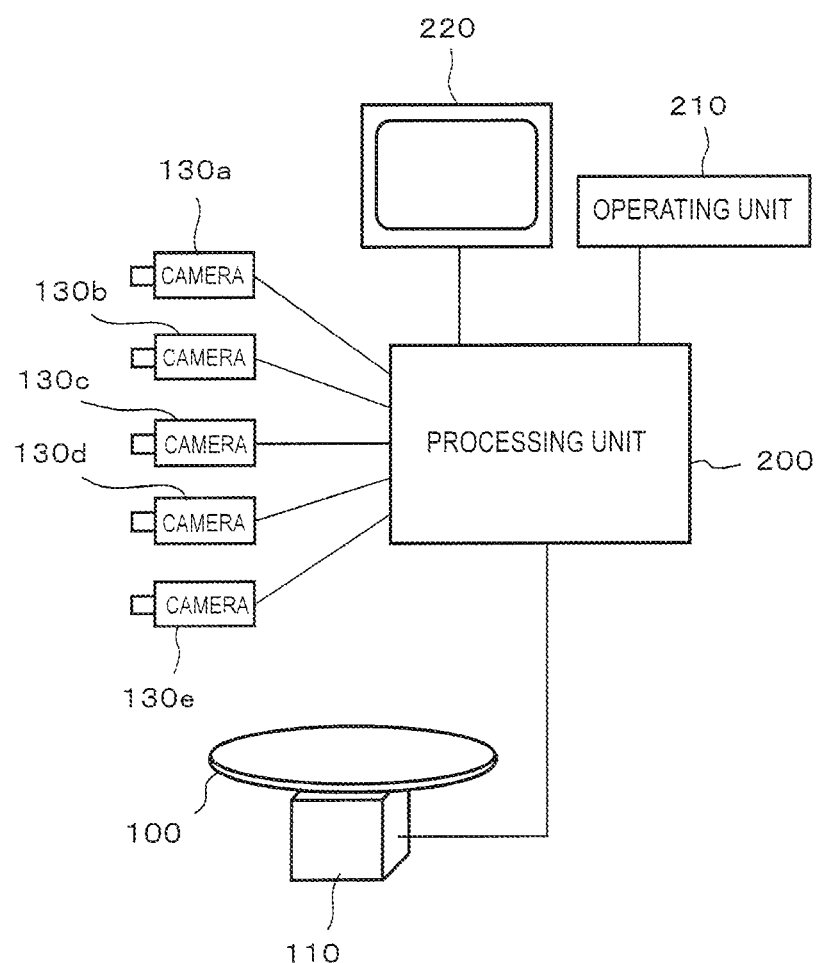
FIG. 3 A block diagram schematically showing main parts of processing system of an edge inspection apparatus of a semiconductor wafer as an inspection apparatus of a disk-shaped substrate according to an embodiment of the present invention.

The processing system of the above-mentioned edge inspection apparatus is configured as shown in FIG. 3.

In FIG. 3, the first camera unit 130a to fifth camera unit 130e are connected to a processing unit 200 (image processor) comprised of a computer. The processing unit 200 controls the drive of the rotational drive motor 110 so that the stage 100 on which the semiconductor wafer 10 is set by an alignment mechanism in a horizontal state is rotated by a predetermined speed and processes image signals successively output from the first camera unit 130a to fifth camera unit 130e. The processing unit 200 has an operating unit 210 and display unit 220 connected to it, executes various types of processing based on signals from the operating unit 210 operated by an operator, and displays images based on image data generated from the image signals, information showing inspection results obtained by processing the image data, etc. on the display unit 220.

Figure 4:
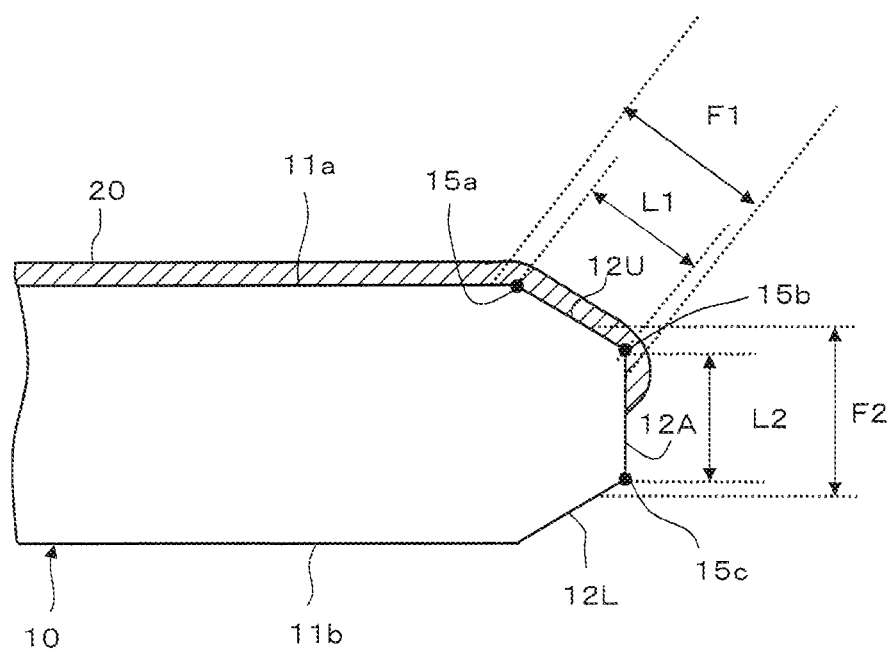
FIG. 4 A view showing field of views F1 and F2 and wafer image capture ranges L1 and L2 of a first camera unit and a second camera unit on a semiconductor wafer having a film layer formed on its surface.

In this regard, the surface of the wafer 10 forming the object under inspection in the above-mentioned edge inspection apparatus is, for example, as shown in FIG. 4, formed with a film layer 20 (insulating film layer, conductive film layer, resist film layer, etc.) Note that, FIG. 4 shows a cross-section of a certain position of the wafer 10 in the circumferential direction Ds, specifically, a rotational angle position θi (position in circumferential direction) away from the reference position (for example, notch 13 shown in FIG. 21A). Further, in FIG. 4, the thickness of the film layer 20 is shown exaggerated. In actuality, compared with the thickness of the wafer 10 shown, the thickness of the film layer 20 is considerably smaller than that shown (same in later mentioned FIG. 7).

In FIG. 4, in the field of view F1 of the first camera unit 130a, the actual capturable range L1 in the direction traversing the circumferential direction of the wafer 10 under inspection is substantially the range between a boundary between the upper outer circumference bevel surface 12U and upper surface 11a, constituting a first boundary edge 15a, and a boundary between the upper outer circumference bevel surface 12U and the outer circumference end face 12A, constituting a second boundary edge 15b, that is, approximately matches the range of the upper outer circumference bevel surface 12U. This is because the first camera unit 130a arranged so as to frontally face the upper outer circumference bevel surface 12U does not frontally face the upper surface 11a and outer circumference end face 12A and, even if the field of view F1 of the first camera unit 130a spreads slightly to the upper surface 11a side and outer circumference end face 12A side under the illumination and other optical conditions suitable for capturing an image of the upper outer circumference bevel surface 12U, the upper surface 11a and outer circumference end face 12A will not be clearly caught compared with the upper outer circumference bevel surface 12U. Therefore, on the captured image, an image part corresponding to the upper surface 11a or outer circumference end face 12A can be differentiated as an image part at the outside of the image part corresponding to the upper outer circumference bevel surface 12U.

Figure 5A:
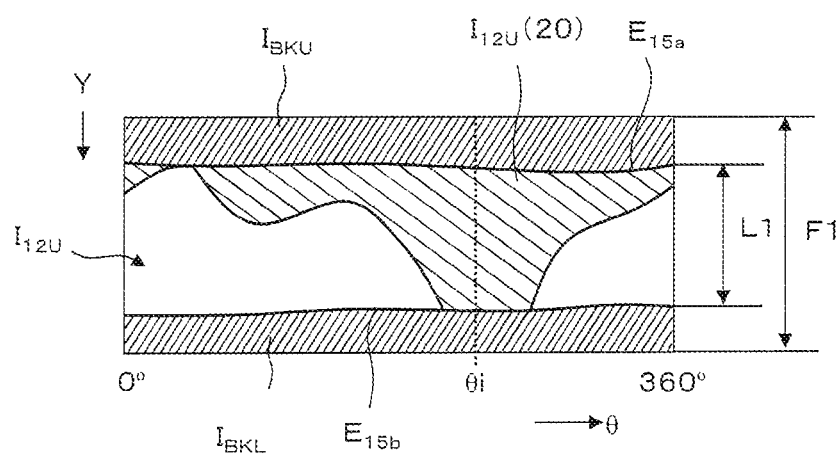
FIG. 5A A view showing an example of an image obtained by the first camera unit capturing the image of an upper outer circumference bevel surface at an outer circumference part of the semiconductor wafer shown in FIG. 4.

As a result, the captured image corresponding to the field of view F1 extending corresponding to one turn (360 degrees) from a reference position (0 degree) in the circumferential direction of the wafer 10 obtained from the image signals successively output from the first camera unit 130a, for example, becomes as shown in FIG. 5A. In FIG. 5A, this captured image includes an upper outer circumference bevel surface image part $I_{12U}$ corresponding to the upper outer circumference bevel surface 12U (capturable range L1). The two sides in the direction traversing the circumferential direction (θ direction) become the outer image parts $I_{BUK}$ and $I_{BKL}$. One outer image part $I_{BKU}$ corresponds to the upper surface outer circumference part which the upper outer circumference bevel surface 12U adjoins. The boundary line $E_{15a}$ between the upper outer circumference bevel surface image part $I_{12U}$ and this outer image part $I_{BKU}$ corresponds to the boundary between the upper outer circumference bevel surface 12U and the upper surface 11a, constituting the first boundary edge 15a (see FIG. 4). Further, the other outer image part $I_{BKL}$ corresponds to the outer circumference end face 12A. The boundary line $E_{15b}$ between the upper outer circumference bevel surface image part $I_{12U}$ and this outer image part $I_{BKL}$ corresponds to the boundary between the upper outer circumference bevel surface 12U and outer circumference end face 12A, constituting the second boundary edge 15b (see FIG. 4). Further, on the upper outer circumference bevel surface image part $I_{12U}$, a film layer image part $I_{12U}(20)$ corresponding to the film layer 20 is formed.

Returning to FIG. 4, in the field of view F2 of the second camera unit 130b, the actual capturable range L2 in the direction traversing the circumferential direction of the wafer 10 being captured is substantially the range between the boundary between the outer circumference end face 12A and upper outer circumference bevel surface 12U, constituting the second boundary edge 15b, and the boundary between the outer circumference end face 12A and lower outer circumference bevel surface 12L, constituting a third boundary edge 15c, and substantially matches with the range of the outer circumference end face 12A. This also, in the same way as above, is due to the fact that the second camera unit 130b arranged so as to frontally face the outer circumference end face 12A does not frontally face the upper outer circumference bevel surface 12U and lower outer circumference bevel surface 12L and, even if the field of view F2 of the second camera unit 130b spreads slightly to the upper outer circumference bevel surface 12U side and lower outer circumference bevel surface 12L side under the illumination and other optical conditions suitable for capturing an image of the outer circumference end face 12A, the upper outer circumference bevel surface 12U and the lower outer circumference bevel surface 12L will not be clearly caught compared with the outer circumference end face 12A. In this case as well, on the captured image, an image part corresponding to the upper outer circumference bevel surface 12U or the lower outer circumference bevel surface 12L can be differentiated as an image part at the outside of the image part corresponding to the outer circumference end face 12A.

Figure 5B:
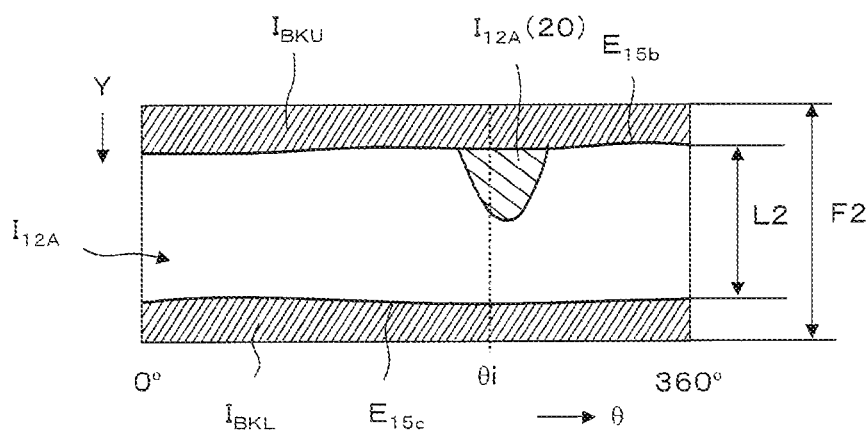
FIG. 5B A view showing an example of an image obtained by the second camera unit capturing the image of an outer circumference end face at an outer circumference part of the semiconductor wafer shown in FIG. 4.

As a result, the captured image corresponding to the field of view F2 extending corresponding to the circumferential direction of the wafer 10 obtained from the image signals successively output from the second camera unit 130b, for example, becomes as shown in FIG. 5B. In FIG. 5B, this captured image includes the outer circumference end face image part $I_{12A}$ corresponding to the outer circumference end face 12A (capturable range L2). The two sides in the direction traversing the circumferential direction (θ direction) become the outer image parts $I_{BKU}$ and $I_{BKL}$. One outer image part $I_{BKU}$ corresponds to the upper outer circumference bevel surface 12U. The boundary line $E_{15b}$ between the outer circumference end face image part $I_{12A}$ and this outer image part $I_{BKU}$ corresponds to the boundary between the outer circumference end face 12A and upper outer circumference bevel surface 12U, constituting the second boundary edge 15b (see FIG. 4). Further, the other outer image part $I_{BKL}$ corresponds to the lower outer circumference bevel surface 12L. The boundary line $E_{15c}$ of the outer circumference end face image part $I_{12A}$ and this outer image part $I_{BKL}$ corresponds to the boundary between the outer circumference end face 12A and lower outer circumference bevel surface 12L, constituting the third boundary edge 15c (see FIG. 4). Further, on the outer circumference end face image part $I_{12A}$, a film layer image part $I_{12A}(20)$ corresponding to the film layer 20 is formed.

In this regard, in the captured image corresponding to the field of view F1 of the first camera unit 130a (see FIG. 5A), the boundary lines $E_{15a}$ and $E_{15b}$ between the upper outer circumference bevel surface image part $I_{12U}$ and outer image parts $I_{BKU}$ and $I_{BKL}$ correspond to the boundary between the upper outer circumference bevel surface 12U and upper surface 11a, constituting the first boundary edge 15a, and the boundary between the upper outer circumference bevel surface 12U and outer circumference end face 12A, constituting the second boundary edge 15b, so the longitudinal direction positions (Y) expressing positions in a direction traversing this circumferential direction are originally expressed the same at the different positions along the circumferential direction, that is, appear as a straight line on the captured image. Further, in the captured image corresponding to the field of view F2 of the second camera unit 130b (see FIG. 5B) as well, the boundary lines $E_{15b}$ and $E_{15c}$ between the outer circumference end face image part $I_{12A}$ and the outer image parts $I_{BKU}$ and $I_{BKL}$ originally should appear as straight lines on the captured image.

However, these boundary lines $E_{15a}$, $E_{15b}$, and $E_{15c}$ on the captured image, as shown in FIG. 5A and FIG. 5B, do not become straight. That is, the boundary lines $E_{15a}$, $E_{15b}$, and $E_{15c}$ fluctuate in the longitudinal direction positions (Y) at different positions (θ) along the circumferential direction. This is due to the following reasons.

Figure 6:
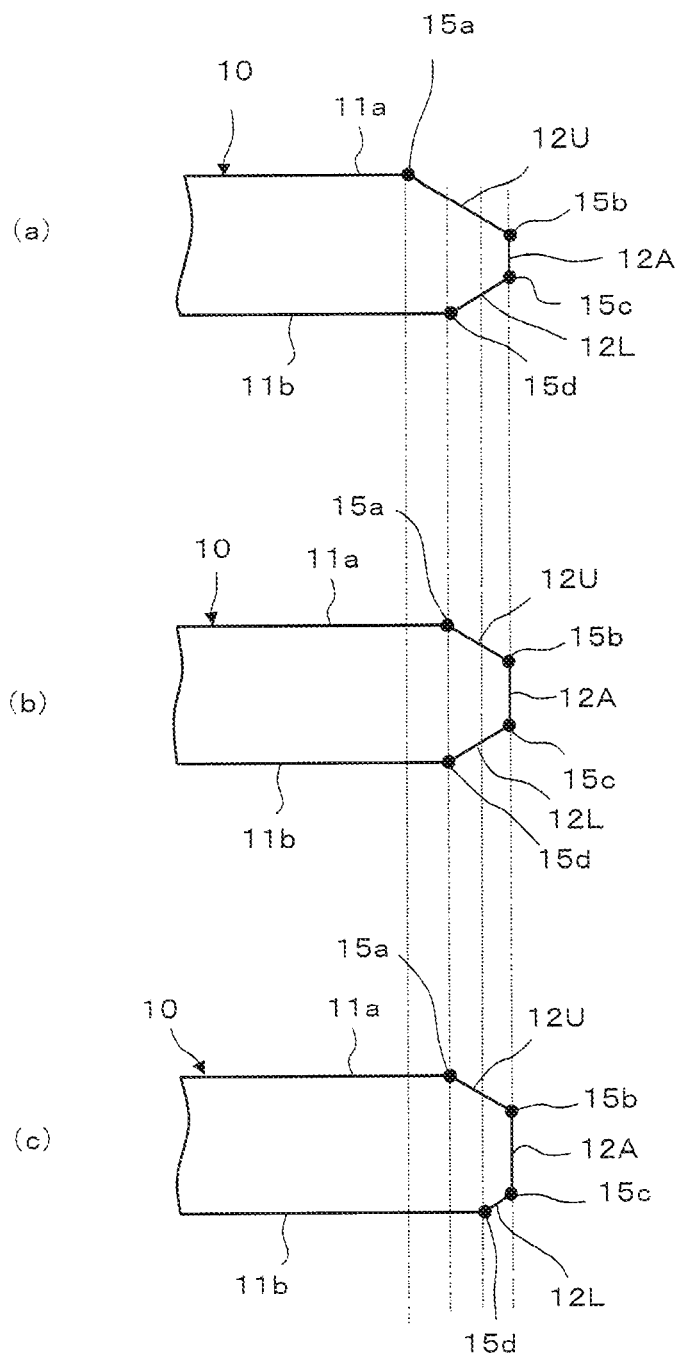
FIG. 6 A view showing variations in shapes of the outer circumference part of a semiconductor wafer.

The upper outer circumference bevel surface 12U, the outer circumference end face 12A, and the lower outer circumference bevel surface 12L at the outer circumference part of the wafer 10 can fluctuate in various ways in width and angle of inclination at different positions (θ) along the circumferential direction due to machining precision etc. for example as shown in (a), (b), and (c) of FIG. 6. For this reason, the positions in the diametrical direction of the first boundary edge 15a, second boundary edge 15b, third boundary edge 15c, and fourth boundary edge 15d forming boundaries with the adjoining surfaces 11a, 12U, 12A, 12L, and 11b at the wafer 10 can fluctuate at the different positions in the circumferential direction. Since, in this way, the positions of the boundary edges 15a, 15b, and 15c forming boundaries of the outer circumference part of the wafer 10 with adjoining surfaces fluctuate, the boundary lines $E_{15a}$, $E_{15b}$, and $E_{15c}$ between the surface image parts on the captured image corresponding to the boundary edges (upper outer circumference bevel surface image part $I_{12U}$, outer circumference end face image part $I_{12A}$, etc.) and outer image parts $I_{BKU}$ and $I_{BKL}$ will not become straight on the captured images (constant longitudinal direction positions at different positions in the circumferential direction).

This phenomenon can occur not only with respect to each wafer 10, but also between individual wafers 10.

Due to this situation, it is difficult to precisely quantitatively evaluate (inspect) the positions of formation of the film layer 20 at the different surfaces (upper surface 11a, upper outer circumference bevel surface 12U, outer circumference end face 12A, lower outer circumference bevel surface 12L, and lower surface 11b) directly from the captured images such as shown in FIG. 5A and FIG. 5B, for example, the edge lines of the film layer 20.

An inspection apparatus according to an embodiment of the present invention is designed to be able to precisely quantitatively evaluate the positions of formation of film layers on a wafer surface. This will be explained in detail below.

Figure 7:
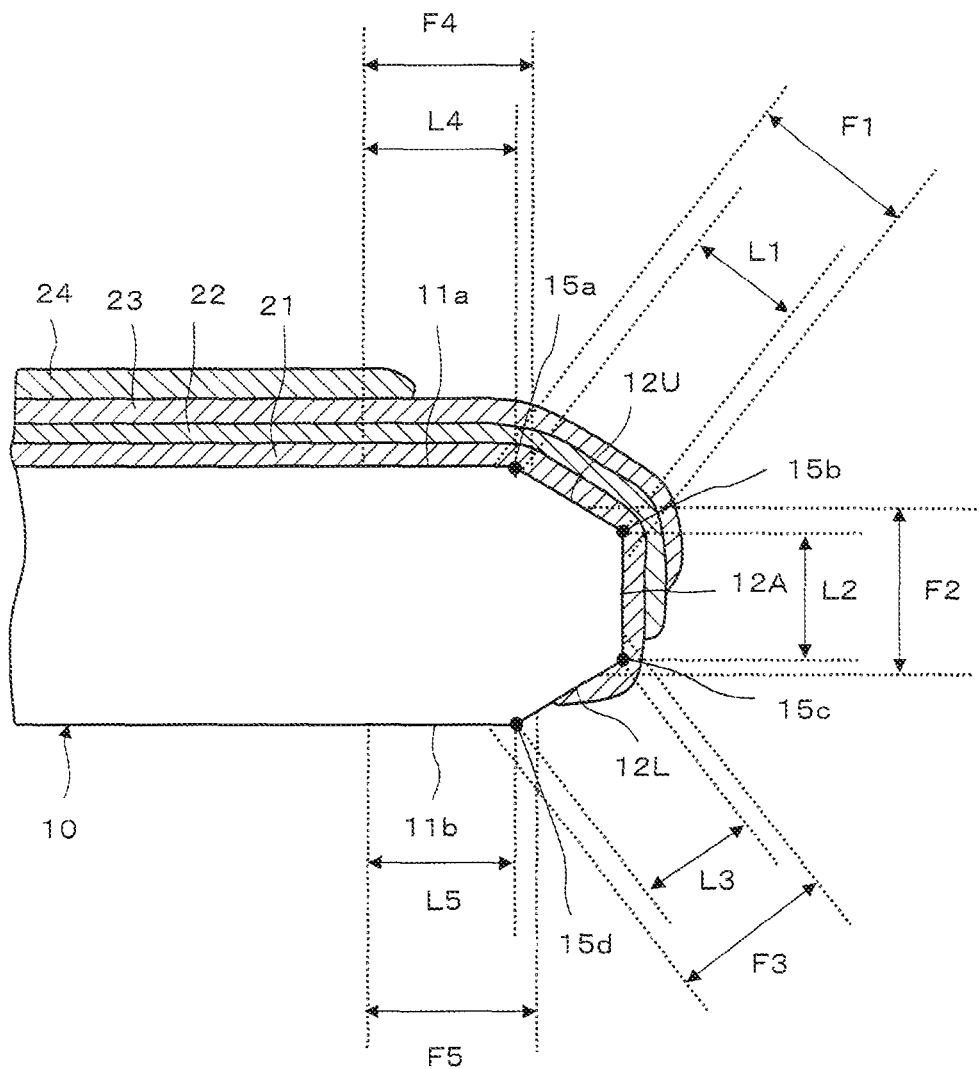
FIG. 7 A view showing the field of views and wafer image capture ranges of five camera units for a semiconductor wafer having four film layers of a first film layer to fourth film layer formed on its surface.

The wafer 10 under inspection, for example, as shown in FIG. 7, has four film layers 21, 22, 23, and 24 formed on its surface. At a certain position (θ) along the circumferential direction of the wafer 10, as shown in FIG. 7, the first film layer 21 runs from the upper surface 11a over the upper outer circumference bevel surface 12U and outer circumference end face 12A and reaches the lower outer circumference bevel surface 12L. The second film layer 22 is laid over the first film layer 21 and runs from the upper surface 11a of the wafer 10 over the upper outer circumference bevel surface 12U and reaches the outer circumference end face 12A. The third film layer 23 is laid over the second film layer 22 and runs from the upper surface 11a of the wafer 10 over the upper outer circumference bevel surface 12U and reaches the outer circumference end face 12A. Further, the fourth film layer 24 is laid over the third film layer 23 on the upper surface 11a without reaching the upper outer circumference bevel surface 12U of the wafer 10.

Near this wafer 10, five camera units 130a to 130e are arranged in the same way as shown in FIG. 2. That is, the field of view F1 of the first camera unit 130a frontally facing the upper outer circumference bevel surface 12U includes the upper outer circumference bevel surface 12U and spreads slightly to the upper surface 11a side and outer circumference end face 12A side. The range between the first boundary edge 15a and second boundary edge 15b corresponding to the upper outer circumference bevel surface 12U becomes the capturable range L1 of the first camera unit 130a. The field of view F2 of the second camera unit 130b frontally facing the outer circumference end face 12A includes the outer circumference end face 12A and spreads slightly to the upper outer circumference bevel surface 12U side and lower outer circumference bevel surface 12L side. The range between the second boundary edge 15b and third boundary edge 15c corresponding to the outer circumference end face 12A becomes the capturable range L2 of the second camera unit 130b. Further, the field of view F3 of the third camera unit 130c frontally facing the lower outer circumference bevel surface 12L includes the lower outer circumference bevel surface 12L and spreads slightly to the outer circumference end face 12A side and lower surface 11b side. The range between the third boundary edge 15c and fourth boundary edge 15d corresponding to the lower outer circumference bevel surface 12L becomes the capturable range L3 of the third camera unit 130c.

Furthermore, the field of view F4 of the fourth camera unit 130d frontally facing the upper surface outer circumference part (region of upper surface 11a adjoining upper outer circumference bevel surface 12U) includes the upper surface outer circumference part and spreads slightly to the upper outer circumference bevel surface 12U side. The range from the first boundary line part 15a to the reverse side limit of the field of view F4 corresponding to the upper surface outer circumference part becomes the capturable range L4 of the fourth camera unit 130d. Further, the field of view F5 of the fifth camera unit 130e frontally facing the lower surface outer circumference part (region of lower surface 11b adjoining lower outer circumference bevel surface 12L) includes the lower surface outer circumference part and spreads slightly to the lower outer circumference bevel surface 12L side. The range from the fourth boundary edge 15d corresponding to the lower surface outer circumference part to the reverse side limit of the field of view F5 becomes the capturable range L5 of the fifth camera unit 130e.

Figure 8:
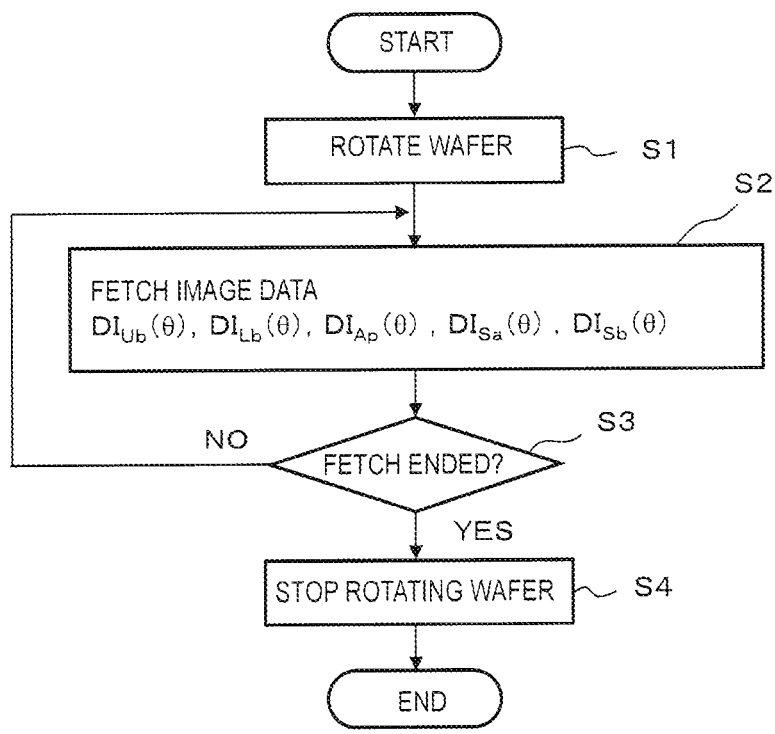
FIG. 8 A flowchart showing processing at a processing unit in the processing apparatus shown in FIG. 3 (part 1).
Figure 9:
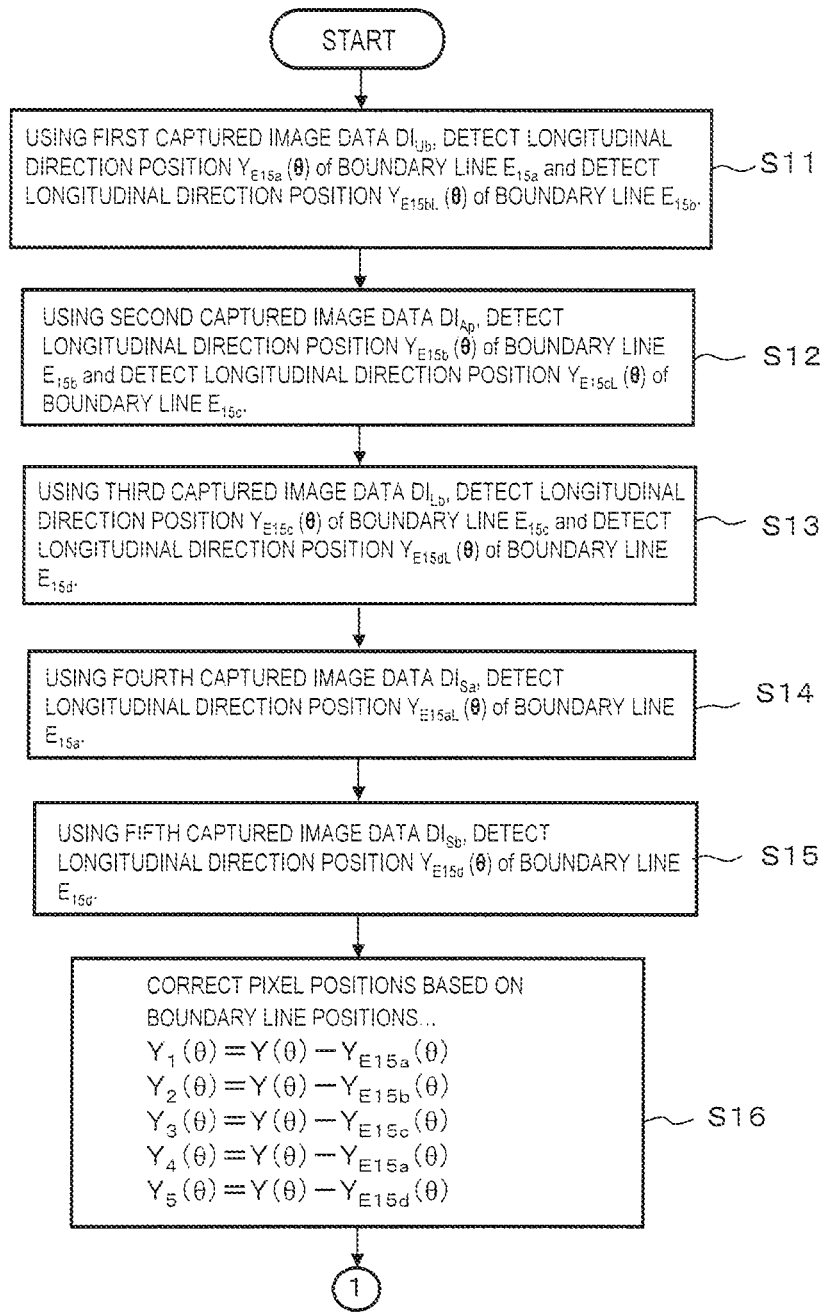
FIG. 9 A flowchart showing processing at a processing unit in the processing system shown in FIG. 3 (part 2).
Figure 10:
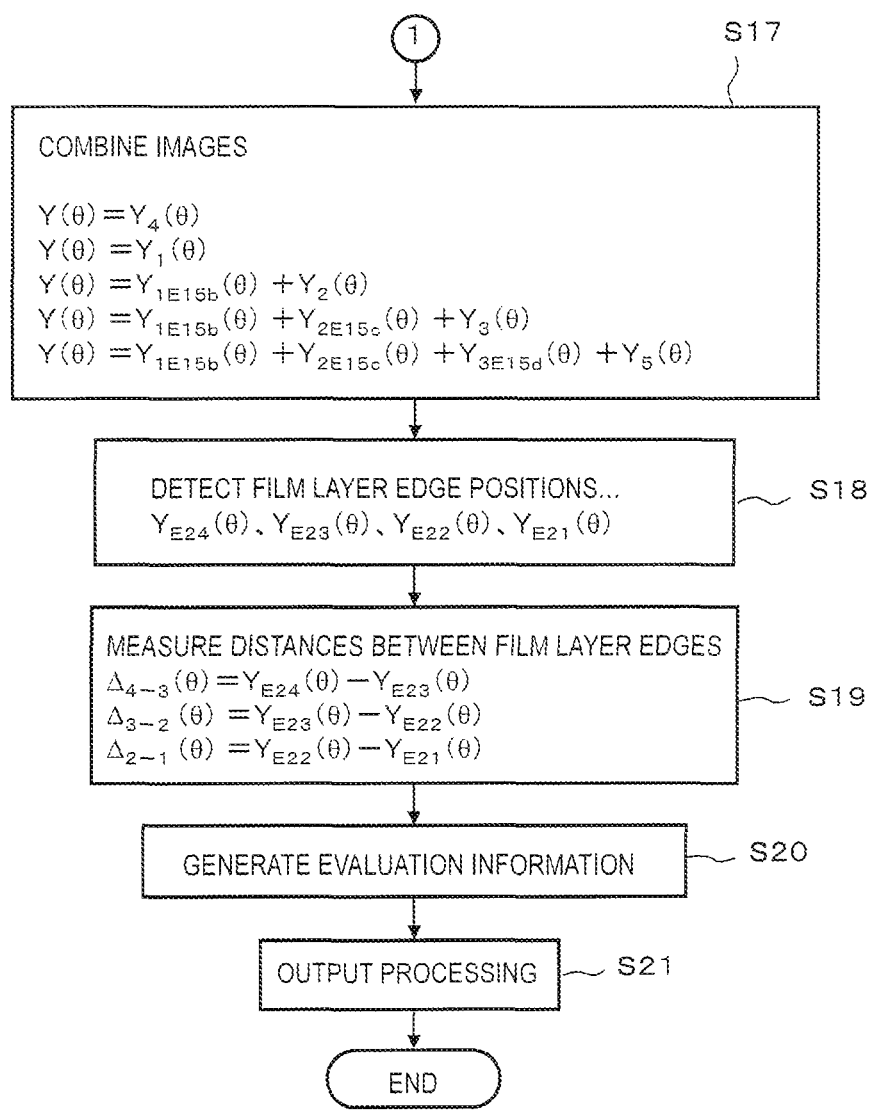
FIG. 10 A flowchart showing processing at a processing unit in the processing system shown in FIG. 3 (part 3).

The processing unit 200 successively receiving as input the image signals output from the camera units 130a to 130e set so that the fields of view F1 to F5 become as explained above performs processing in accordance with the routine shown in FIG. 8 to FIG. 10.

In FIG. 8, the processing unit 200 controls the drive of the rotational drive motor 110 to make the stage 100 rotate in a predetermined direction by a predetermined speed (S1). Due to this, the wafer 10 set on the stage 100 rotates. In the process of the wafer 10 rotating, the processing unit 200 uses the image signals successively output from the first camera unit 130a, second camera unit 130b, third camera unit 130c, fourth camera unit 130d, and fifth camera unit 130e to generate captured image data expressing captured images corresponding to the fields of view F1 to F5 extending in the circumferential direction of the wafer 10. That captured image data is stored in a predetermined memory (S2).

Specifically, based on the image signals from the first camera unit 130a, first captured image data $DI_{Ub(\theta)}$ expressing a first captured image extending corresponding to the circumferential direction of the wafer 10 and corresponding to the field of view F1 including the upper outer circumference bevel surface 12U of one turn of the same (0 degree to 360 degrees) is generated; based on the image signals from the second camera unit 130b, similarly, second captured image data $DI_{Ap(\theta)}$ expressing a second captured image corresponding to the field of view F2 including the outer circumference end face 12A of one turn of the wafer 10 is generated; and, based on the image signals from the third camera unit 130c, similarly, third captured image data $ID_{Lb(\theta)}$ expressing a third captured image corresponding to the field of view F3 including the lower outer circumference bevel surface 12L of one turn of the wafer 10 is generated. Furthermore, based on the image signals from the fourth camera unit 130d, fourth captured image data $DI_{Sa}$ expressing a fourth captured image corresponding to the field of view F4 including the upper surface outer circumference part of one turn of the wafer 10 (region of upper surface 11a adjoining upper outer circumference bevel surface 12U) is generated. Further, based on the image signals from the fifth camera unit 130e, fifth captured image data $DI_{Sb(\theta)}$ expressing a fifth captured image corresponding to the field of view F5 including the lower surface outer circumference part of one turn of the wafer 10 (region of lower surface 1ib adjoining lower outer circumference bevel surface 12L) is generated.

The captured image data are expressed as darkness (brightness) information of pixel points determined by circumferential direction positions (θ) and longitudinal direction positions Y expressing positions in a direction traversing the circumferential direction (for example, perpendicularly intersecting it). The origin of the longitudinal direction positions Y can be freely determined in the processing unit 200. For example, it is possible to make the end point on the captured image corresponding to one limit point in the direction traversing the circumferential direction in the field of view the origin (Y=0) of the longitudinal direction positions Y.

The processing unit 200, when obtaining the captured image data $ID_{Ub}$, $ID_{Ap}$, $ID_{Lb}$, $ID_{Sa}$, and $ID_{Sb}$ of one turn of the wafer 10 (S3, YES), makes the rotational drive motor 110 stop to stop the rotation of the wafer 10 (S4) and ends the processing relating to acquisition of captured images.

Figure 11A:
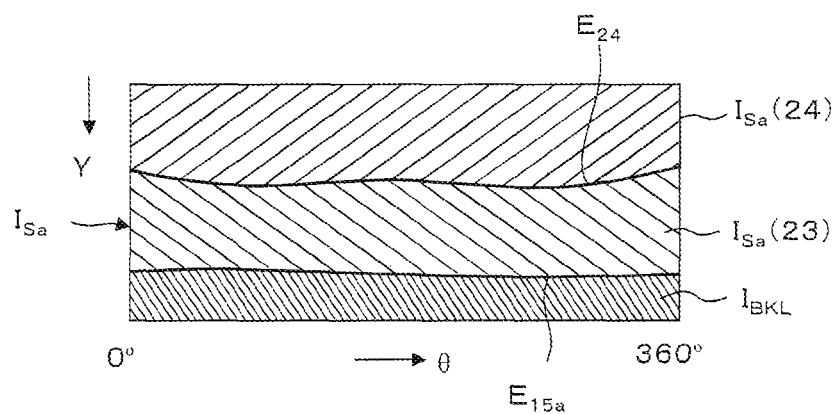
FIG. 11A A view showing an example of an image obtained by the fourth camera unit capturing the image of an upper surface at the outer circumference part of the semiconductor wafer shown in FIG. 7.
Figure 11B:
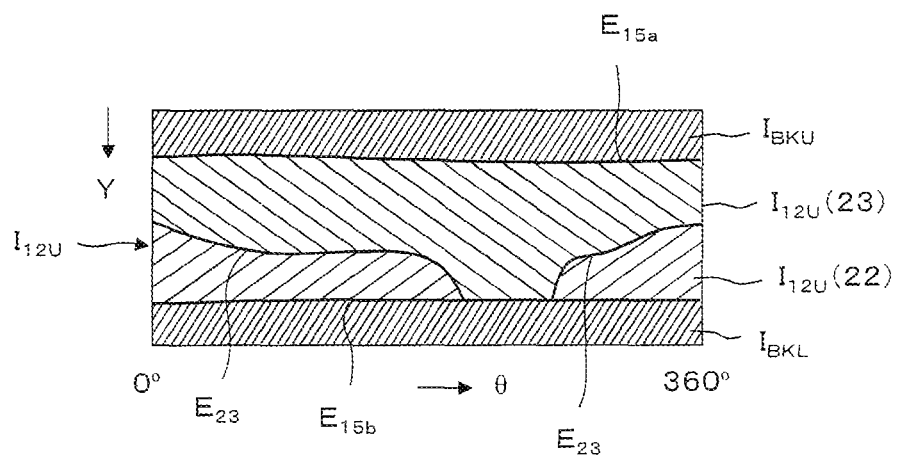
FIG. 11B A view showing an example of an image obtained by the first camera unit capturing the image of an upper outer circumference bevel surface at the outer circumference part of the semiconductor wafer shown in FIG. 7.
Figure 12A:
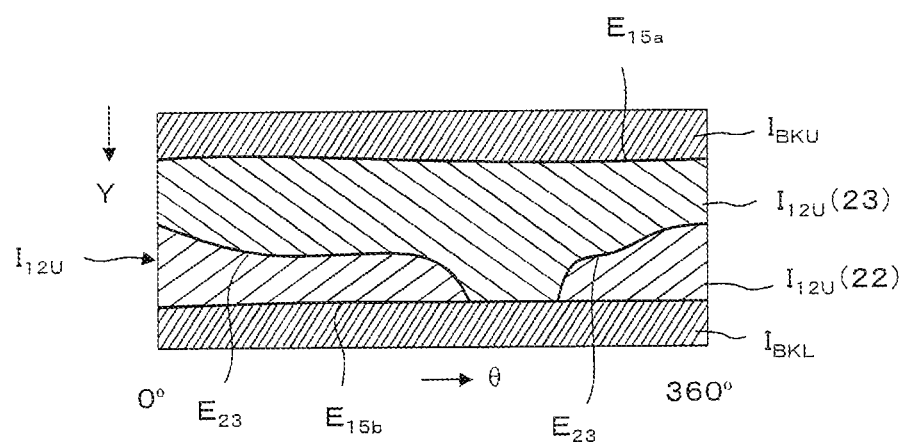
FIG. 12A A view showing an example of an image obtained by the first camera unit capturing the image of an upper outer circumference bevel surface at the outer circumference part of the semiconductor wafer shown in FIG. 7.

The first captured image expressed by the first captured image data $DI_{Ub}$, for example, becomes as shown in FIG. 11B and FIG. 12A. This first captured image includes an upper outer circumference bevel surface image part $I_{12U}$. The two sides in the direction traversing the circumferential direction form the outer image parts $I_{BUK}$ and $I_{BKL}$. One outer image part $I_{BKU}$ corresponds to the upper surface outer circumference part which the upper outer circumference bevel surface 12U adjoins. The boundary line $E_{15a}$ between the upper outer circumference bevel surface image part $I_{12U}$ and this outer image part $I_{BKU}$ corresponds to the boundary between the upper outer circumference bevel surface 12U and upper surface 11a, constituting the first boundary edge 15a (see FIG. 7). Further, the other outer image part $I_{BKL}$ corresponds to the outer circumference end face 12A. The boundary line $E_{15b}$ between the upper outer circumference bevel surface image part $I_{12U}$ and this outer image part $I_{BKL}$ corresponds to the boundary of the upper outer circumference bevel surface 12U and outer circumference end face 12A, constituting the second boundary edge 15b (see FIG. 7). On the upper outer circumference bevel surface image part $I_{12U}$, a second film layer image part $I_{12U}$ (22) corresponding to the second film layer 22 and a third film layer image part $I_{12U}$ (23) corresponding to the third film layer 23 are formed. Further, at this first captured image, an edge line $E_{23}$ of a third film layer image part $I_{12U}$ (23) corresponding to the third film layer 23 laid over the second film layer 22 appears.

Figure 12B:
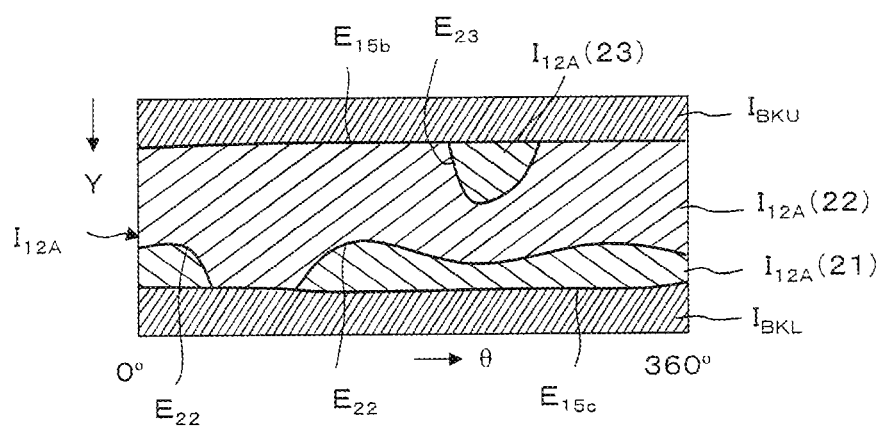
FIG. 12B A view showing an example of an image obtained by the second camera unit capturing the image of the outer circumference end face at the outer circumference part of the semiconductor wafer shown FIG. 7.
Figure 13A:
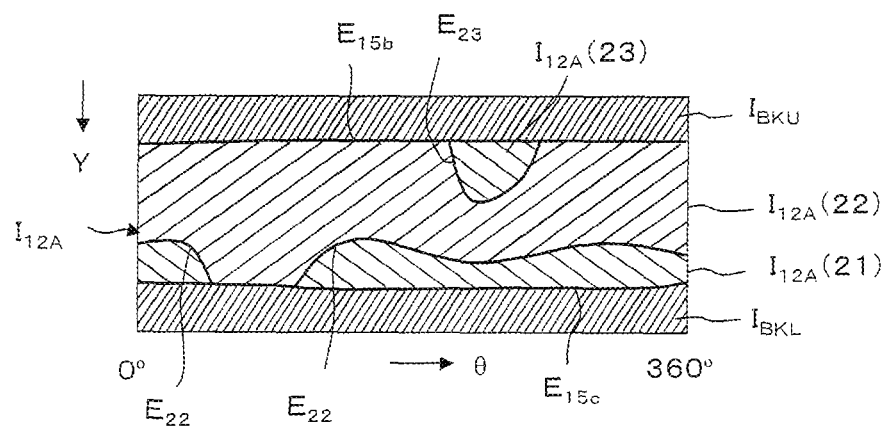
FIG. 13A A view showing an example of an image obtained by the second camera unit capturing the image of the outer circumference end face at the outer circumference part of the semiconductor wafer shown FIG. 7.

The second captured image expressed by the second captured image data $DI_{Ap}$, for example, becomes as shown in FIG. 12B and FIG. 13A. This second captured image includes an outer circumference end face image part $I_{12A}$. The two sides in the direction traversing the circumferential direction form the outer image parts $I_{BUK}$ and $I_{BKL}$. One outer image part $I_{BKU}$ corresponds to the upper outer circumference bevel surface 12U which the outer circumference end face 12A adjoins. The boundary line $E_{15b}$ of the outer circumference end face image part $I_{12A}$ and this outer image part $I_{BKU}$ corresponds to the boundary between the outer circumference end face 12A and upper outer circumference bevel surface 12U, constituting the second boundary edge 15b (see FIG. 7). Further, the other outer image part $I_{BK}$ corresponds to the lower outer circumference bevel surface 12L. The boundary line $E_{15c}$ between the outer circumference end face image part $I_{12A}$ and this outer image part $I_{BKL}$ corresponds to the boundary between the outer circumference end face 12A and lower outer circumference bevel surface 12L, constituting the third boundary edge 15c (see FIG. 7). On the outer circumference end face image part $I_{12A}$, a first film layer image part (21) corresponding to the first film layer 21, a second film layer image part $I_{12A}$ (22) corresponding to the second film layer 22, and a third film layer image part $I_{12A}$ (23) corresponding to the third film layer 23 are formed. Further, at this second captured image, an edge line $E_{22}$ of the second film layer image part $I_{12A}$ (22) corresponding to the second film layer 22 laid over the first film layer 21 and an edge line $E_{23}$ of the third film layer image part $I_{12A}$ (23) corresponding to the third film layer 23 laid over the second film layer 22 appear.

Figure 13B:
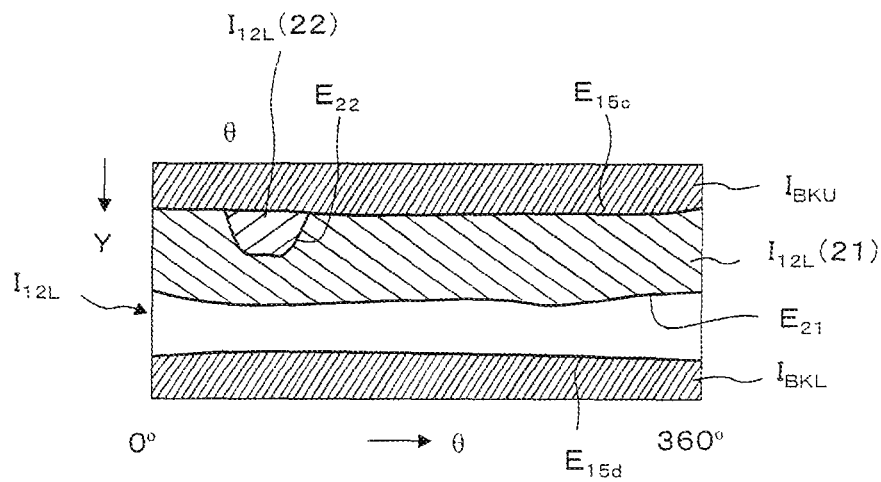
FIG. 13B A view showing an example of an image obtained by the third camera unit capturing the image of the lower outer circumference bevel surface at the outer circumference part of the semiconductor wafer shown FIG. 7.
Figure 14A:
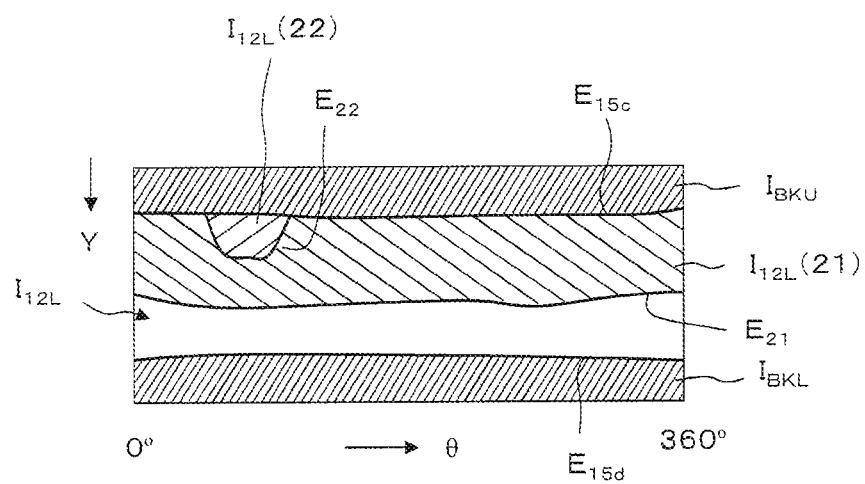
FIG. 14A A view showing an example of an image obtained by the third camera unit capturing the image of the lower outer circumference bevel surface at the outer circumference part of the semiconductor wafer shown FIG. 7.

The third captured image expressed by the third captured image data $DI_{Lb}$, for example, becomes as shown in FIG. 13B and FIG. 14A. This third captured image includes the lower outer circumference bevel surface image part $I_{12L}$. The two sides in the direction traversing the circumferential direction form the outer image parts $I_{BUK}$ and $I_{BKL}$. One outer image part $I_{BKU}$ corresponds to the outer circumference end face 12A which the lower outer circumference bevel surface 12L adjoins. The boundary line $E_{15c}$ between the lower outer circumference bevel surface image part $I_{12L}$ and this outer image part $I_{BKU}$ corresponds to the boundary between the lower outer circumference bevel surface 12L and outer circumference end face 12A, constituting the third boundary edge 15c (see FIG. 7). Further, the other outer image part $I_{BKL}$ corresponds to the lower surface outer circumference part. The boundary line $E_{15d}$ between the lower outer circumference bevel surface image part $I_{12L}$ and this outer image part $I_{BKL}$ corresponds to the boundary between the lower outer circumference bevel surface 12L and lower surface 11b, constituting a fourth boundary edge 15d (see FIG. 7). On the lower outer circumference bevel surface image part $I_{12L}$, a first film layer image part $I_{12L}$ (21) corresponding to the first film layer 21 and a second film layer image part $I_{12L}$ (22) corresponding to the second film layer 22 are formed. Further, at this third captured image, an edge line $E_{21}$ of the first film layer image part $I_{12L}$ (21) and an edge line $E_{22}$ of the second film layer image part $I_{12L}$ (22) corresponding to the second film layer 22 laid over the first film layer 21 appear.

The fourth captured image expressed by the fourth captured image data $DI_{Sa}$ becomes, for example, as shown in FIG. 11A. This fourth captured image includes an upper surface image part $I_{Sa}$ (corresponding to the region of the upper surface 11a adjoining the upper outer circumference bevel surface 12U). One side in the direction traversing the circumferential direction forms the outer image part $I_{BKL}$. This outer image part $I_{BKL}$ corresponds to the upper outer circumference bevel surface 12U. The boundary line $E_{15a}$ between the upper surface image part $I_{Sa}$ and this outer image part $I_{BKL}$ corresponds to the boundary of the upper surface 11a and upper outer circumference bevel surface 12U, constituting the first boundary edge 15a (see FIG. 7). On the upper surface image part $I_{Sa}$, a third film layer image part $I_{Sa}$ (23) corresponding to the third film layer 23 and a fourth film layer image part $I_{Sa}$ (24) corresponding to the fourth film layer 24 are formed. Further, at this fourth captured image, an edge line $E_{24}$ of the fourth film layer image part $I_{Sa}$ (24) corresponding to the fourth film layer 24 laid over the third film layer 23 appears.

Figure 14B:
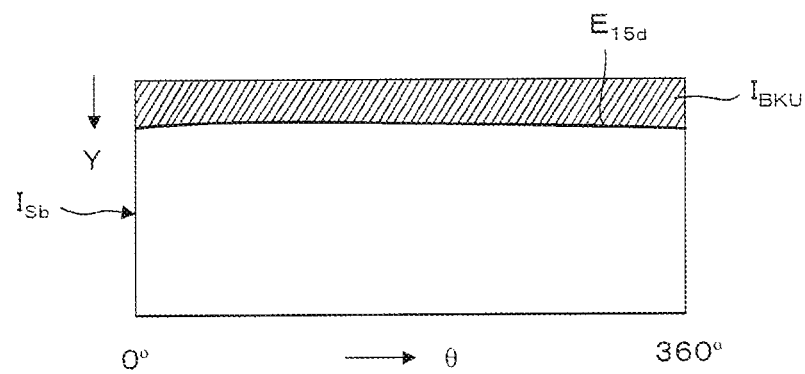
FIG. 14B A view showing an example of an image obtained by the fifth camera unit capturing the image of the lower surface at the outer circumference part of the semiconductor wafer in the outer circumference part of the semiconductor wafer shown FIG. 7.

The fifth captured image expressed by the fifth captured image data $DI_{Sb}$, for example, becomes as shown in FIG. 14B. This fifth captured image includes the bottom surface image part $I_{Sb}$ (corresponding to the region of the lower surface 11a adjoining the lower outer circumference bevel surface 12L). One side in the direction traversing the circumferential direction forms the outer image part $I_{BKU}$. This background image part $I_{BKU}$ corresponds to the lower outer circumference bevel surface 12L. The boundary line $E_{15d}$ between the bottom surface image part $I_{Sb}$ and this outer image part $I_{BKU}$ corresponds to the boundary between the lower surface 11b and lower outer circumference bevel surface 12L, constituting the fourth boundary edge 15d (see FIG. 7). Note that, in this example, on the lower surface image part $I_{Sb}$, no image part corresponding to a film layer particularly appears.

The processing unit 200 acquiring the first captured image data $DI_{Ub}$ to fifth captured image data $DI_{Sb}$ according to the routine shown in FIG. 8 next executes processing according to the routine shown in FIG. 9 and FIG. 10.

Figure 16A:
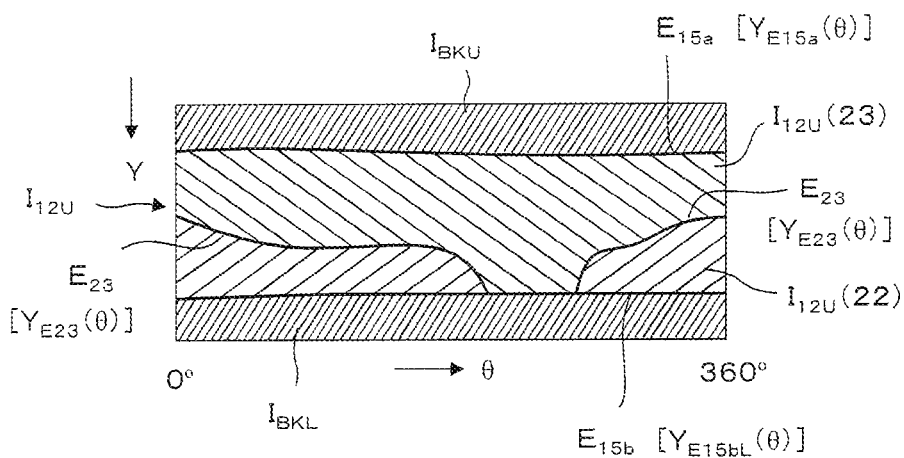
FIG. 16A A view showing positions Y on an image including an edge line $E_{23}$ of a third film layer image and a boundary line $E_{15a}$ corresponding to a first boundary edge 15a and a boundary line $E_{15b}$ corresponding to a second boundary edge 15b of the semiconductor wafer obtained by the first camera unit.
Figure 17A:
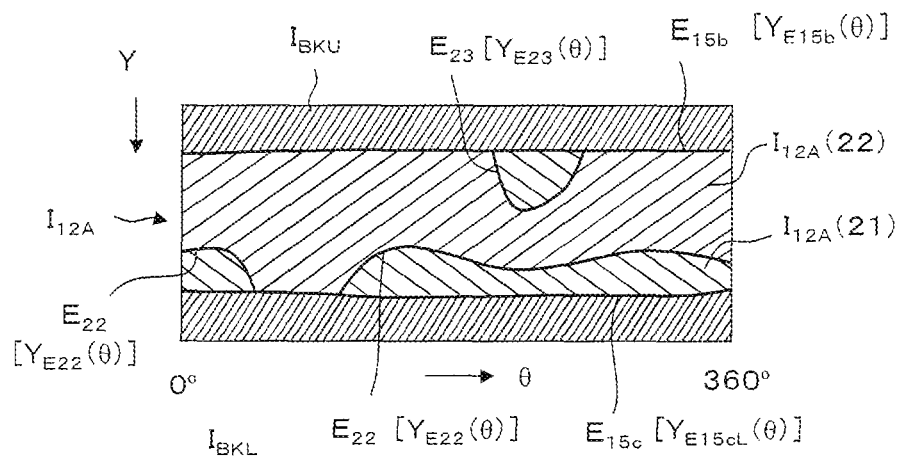
FIG. 17A A view showing positions Y on an image including an edge line $E_{23}$ of a third film layer image, an edge line $E_{22}$ of a second film layer, and a boundary line $E_{15b}$ corresponding to a second boundary edge 15b and a boundary line $E_{15c}$ corresponding to a third boundary edge 15d of the semiconductor wafer obtained by the second camera unit.
Figure 18A:
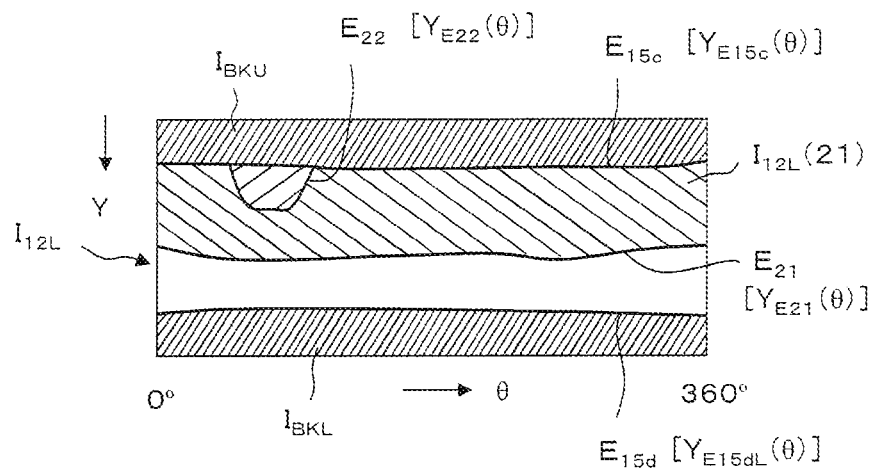
FIG. 18A A view showing positions Y on an image including an edge line $E_{22}$ of a second film layer image, an edge line $E_{21}$ of a first film layer, a boundary line $E_{15c}$ corresponding to a third boundary edge 15c of the semiconductor wafer, and a boundary line $E_{15d}$ corresponding to a fourth boundary edge 15d of the semiconductor wafer obtained by the third camera unit.

First, in FIG. 9, the processing unit 200 extracts from the first captured image data $DI_{Ub}$, as shown in FIG. 16A, the boundary line $E_{15a}$ on the first captured image between the upper outer circumference bevel surface image part $I_{12U}$ and the outer image part $I_{BKU}$ of the upper surface 11a side by a general edge extraction technique and detects the longitudinal direction positions $Y_{E15a(\theta)}$ at the different positions ($\theta$) along the circumferential direction, while similarly extracts the boundary line $E_{15a}$ between the upper outer circumference bevel surface image $I_{12U}$ and outer image part $I_{BKL}$ of the outer circumference end face 12A side and detects the longitudinal direction positions $Y_{E15bL(\theta)}$ at the different positions ($\theta$) along the circumferential direction (S11). The processing unit 200, next, extracts from the second captured image data $DI_{Ap}$, as shown in FIG. 17A, the boundary line $E_{15b}$ on the second captured image between the outer circumference end face image part $I_{12A}$ and outer image part $I_{BKU}$ of the upper outer circumference bevel surface 12U side and detects the longitudinal direction positions $Y_{E15b(\theta)}$ at the different positions ($\theta$) along the circumferential direction, while extracts the boundary line $E_{15c}$ between the outer circumference end face image part $I_{12A}$ and outer image part $I_{BKL}$ of the lower outer circumference bevel surface 12L side and detects the longitudinal direction positions $Y_{E15cL(\theta)}$ at the different positions ($\theta$) along the circumferential direction (S12). Further, the processing unit 200 extracts from the third captured image data $DI_{Lb}$, as shown in FIG. 18A, the boundary line $E_{15c}$ on the third captured image between the lower outer circumference bevel surface image part $I_{12L}$ and outer image part $I_{BKU}$ of the outer circumference end face 12A side and detects the longitudinal direction positions $Y_{E15c(\theta)}$ at the different positions ($\theta$) along the circumferential direction, while extracts the boundary line $E_{15d}$ between the lower outer circumference bevel surface image part $I_{12L}$ and outer image part $I_{BKL}$ on the lower surface 11b side and detects the longitudinal direction positions $Y_{E15dL}(\theta)$ at the different positions ($\theta$) along the circumferential direction (S13).

Figure 15A:
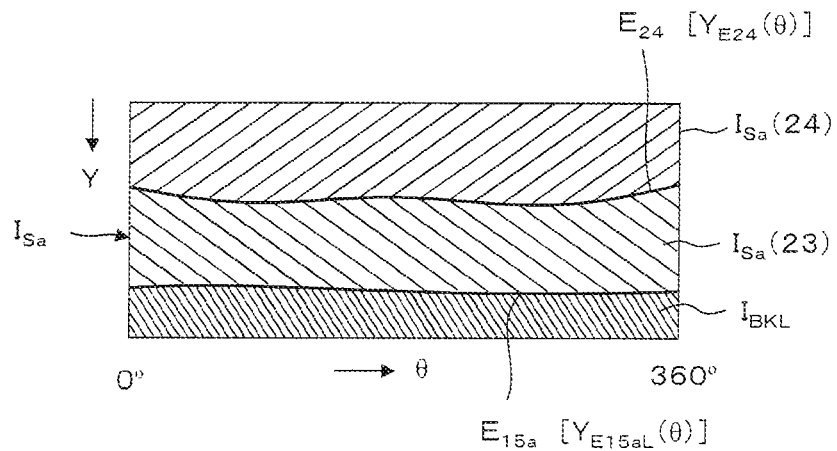
FIG. 15A A view showing positions Y on an image including an edge line $E_{24}$ of a fourth film layer image and a boundary line $E_{15a}$ corresponding to a first boundary edge 15a of the semiconductor wafer obtained by the fourth camera unit.
Figure 19A:
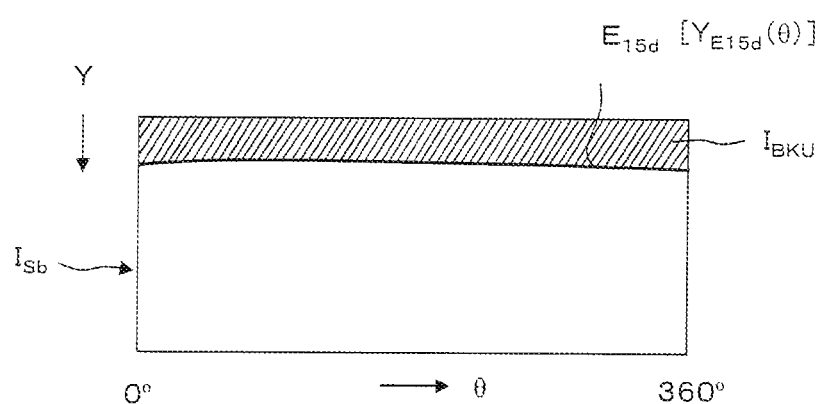
FIG. 19A A view showing positions Y on an image including a boundary line $E_{15d}$ corresponding to a fourth boundary edge 15d of a semiconductor wafer obtained by the fifth camera unit.

Furthermore, the processing unit 200 extracts from the fourth captured image data $DI_{Sa}$, as shown in FIG. 15A, the boundary line $E_{15a}$ on the fourth captured image between the upper surface image part $I_{Sa}$ and outer image part $I_{BKL}$ of the upper outer circumference bevel surface 12U side and detects the longitudinal direction positions $Y_{E15aL}(\theta)$ at the different positions ($\theta$) along the circumferential direction (S14). The processing unit 200, next, extracts from the fifth captured image data $DI_{Sb}$, as shown in FIG. 19A, the boundary line $E_{15d}$ on the fifth captured image between the bottom surface image part $I_{Sb}$ and outer image part $I_{BKU}$ of the lower outer circumference bevel surface 12L side and detects the longitudinal direction positions $Y_{E15d}(\theta)$ at the different positions ($\theta$) along the circumferential direction (S15).

Figure 16B:
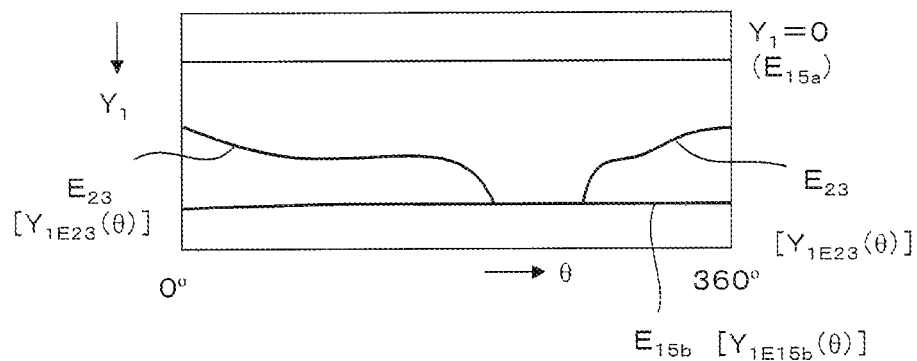

Next, the processing unit 200 performs processing for correction of the image data $DI_{Ub}$, $DI_{Ap}$, $DI_{Lb}$, $DI_{Sa}$, and $DI_{Sb}$ (S16). This correction processing is performed as follows:

The first captured image data $DI_{Ub}$ is corrected so that longitudinal direction positions $Y_1$ ($\theta$) at corresponding positions ($\theta$) along the circumferential direction of the different pixel points on the first captured image are expressed with reference to longitudinal direction positions $Y_{E15a}$ ($\theta$) at different positions ($\theta$) along the circumferential direction of the boundary line $E_{15a}$ between the upper outer circumference bevel surface image part $I_{12U}$ on the corresponding first captured image and its outer image part $I_{BKU}$. Specifically, as shown in FIG. 16B, the longitudinal direction positions $Y_1$ ($\theta$) at the different positions ($\theta$) along the circumferential direction of the boundary line $E_{15a}$ are made zero ($Y_1$=0), and the longitudinal direction positions $Y_1$ ($\theta$) at the corresponding positions ($\theta$) along the circumferential direction of the different pixel points are expressed as distances from the boundary line $E_{15a}$. That is, post-correction longitudinal direction positions $Y_1$ ($\theta$) at the different positions ($\theta$) along the circumferential direction of the different pixel points on the first captured image are expressed by the pre-correction longitudinal direction positions $Y_{E15a}$ ($\theta$) at corresponding positions ($\theta$) along the circumferential direction of the boundary line $E_{15a}$ and the pre-correction longitudinal direction positions Y ($\theta$) at corresponding positions ($\theta$) along the circumferential direction of corresponding pixel points, as $$Y_1(\theta)=Y(\theta)-Y_{E15a}(\theta)$$

Due to such correction of the first captured image data $DI_{Ub}$, as shown in FIG. 16B, the post-correction longitudinal direction positions $Y_{1E15b}$ ($\theta$) at different positions ($\theta$) along the circumferential direction of the boundary line $E_{15b}$ of the other side of the upper outer circumference bevel surface image $I_{12U}$ on the first captured image are similarly expressed using the pre-correction longitudinal direction positions $Y_{E15bL}$ ($\theta$) at corresponding positions ($\theta$) along the circumferential direction of the same boundary line $E_{15b}$ as $$Y_{1E15b}(\theta)=Y_{E15bL}(\theta)-Y_{E15a}(\theta)$$

Further, the post-correction longitudinal direction positions $Y_{1E23}$ ($\theta$) at different positions ($\theta$) along the circumferential direction of the edge line $E_{23}$ of the third film layer image part $I_{12U}$ (23) corresponding to the third film layer 23 on the first captured image (film layer edge position information) are similarly expressed using the pre-correction longitudinal direction positions $Y_{E23}$ ($\theta$) at the corresponding positions ($\theta$) along the circumferential direction of the same edge line $E_{23}$ as $$Y_{1E23}(\theta)=Y_{E23}(\theta)-Y_{E15a}(\theta)$$

Figure 17B:
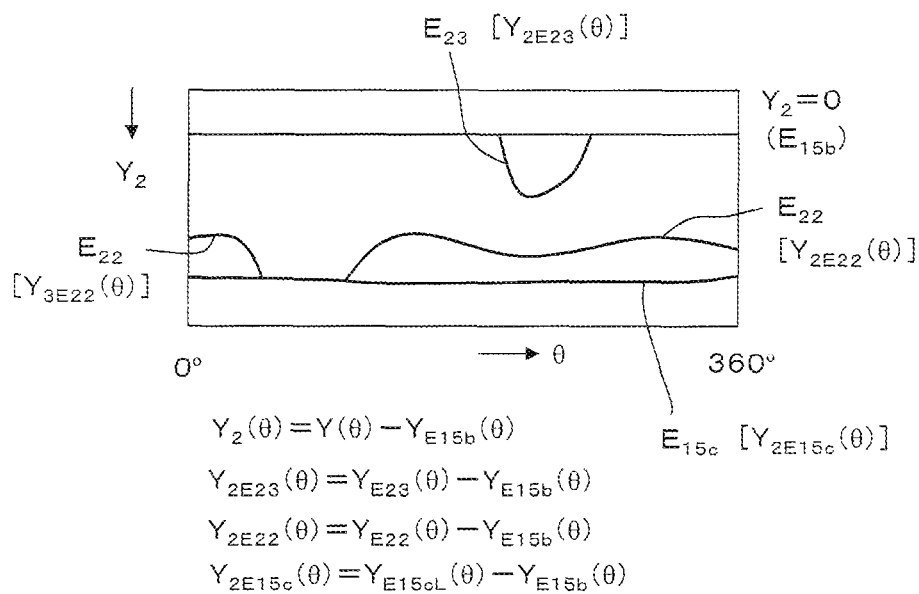
FIG. 17B A view showing corrected positions $Y_2$ on an image correcting the positions Y at FIG. 17A with reference to boundary line positions $Y_{E15b(\theta)}$ corresponding to the second boundary edge 15b.

The second captured image data $DI_{Ap}$ is corrected so that longitudinal direction positions $Y_2$ ($\theta$) at corresponding positions ($\theta$) along the circumferential direction of the different pixel points on the second captured image are expressed with reference to longitudinal direction positions $Y_{E15b}$ ($\theta$) at different positions ($\theta$) along the circumferential direction of the boundary line $E_{15b}$ between the outer circumference end face image part $I_{12A}$ on the corresponding second captured image and its outer image part $I_{BKU}$. Specifically, as shown in FIG. 17B, the longitudinal direction positions $Y_2$ ($\theta$) at the different positions ($\theta$) along the circumferential direction of the boundary line $E_{15b}$ are made zero ($Y_2$=0), and the longitudinal direction positions $Y_2$ ($\theta$) at the corresponding positions ($\theta$) along the circumferential direction of the different pixel points are expressed as distances from the boundary line $E_{15b}$. That is, post-correction longitudinal direction positions $Y_2$ ($\theta$) at the different positions ($\theta$) along the circumferential direction of the different pixel points on the second captured image are similarly expressed by the pre-correction longitudinal direction positions $Y_{E15b}$ ($\theta$) at corresponding positions ($\theta$) along the circumferential direction of the boundary line $E_{15b}$ and the pre-correction longitudinal direction positions Y (θ) at corresponding positions (θ) along the circumferential direction of corresponding pixel points, as $$Y_2(\theta)=Y(\theta)-Y_{E15b}(\theta)$$

Due to such correction of the second captured image data $DI_{Ap}$, as shown in FIG. 17B, the post-correction longitudinal direction positions $Y_{2E15c}(\theta)$ at different positions (θ) along the circumferential direction of the boundary line $E_{15c}$ of the other side of the outer circumference end face image $I_{12A}$ on the second captured image are similarly expressed using the pre-correction longitudinal direction positions $Y_{E15cL}(\theta)$ at corresponding positions (θ) along the circumferential direction of the same boundary line $E_{15c}$ as $$Y_{2E15c}(\theta)=Y_{E15cL}(\theta)-Y_{E15a}(\theta)$$

Further, the post-correction longitudinal direction positions $Y_{2E23}(\theta)$ at different positions (θ) along the circumferential direction of the edge line $E_{23}$ of the third film layer image part $I_{12A}$ (23) corresponding to the third film layer 23 on the second captured image (film layer edge position information) are similarly expressed using the pre-correction longitudinal direction positions $Y_{E23}(\theta)$ at the corresponding positions (θ) along the circumferential direction of the same edge line $E_{23}$ as $$Y_{2E23}(\theta)=Y_{E23}(\theta)-Y_{E15b}(\theta)$$

Further, the longitudinal direction positions $Y_{2E22}(\theta)$ at different positions (θ) along the circumferential direction of the edge line $E_{22}$ of the second film layer image part $I_{12A}$ (22) corresponding to the second film layer 22 (film layer edge position information) are similarly expressed using the pre-correction longitudinal direction positions $Y_{E22}(\theta)$ at the corresponding positions (θ) along the circumferential direction of the same edge line $E_{22}$ as $$Y_{2E22}(\theta)=Y_{E22}(\theta)-Y_{E15b}(\theta)$$

Figure 18B:
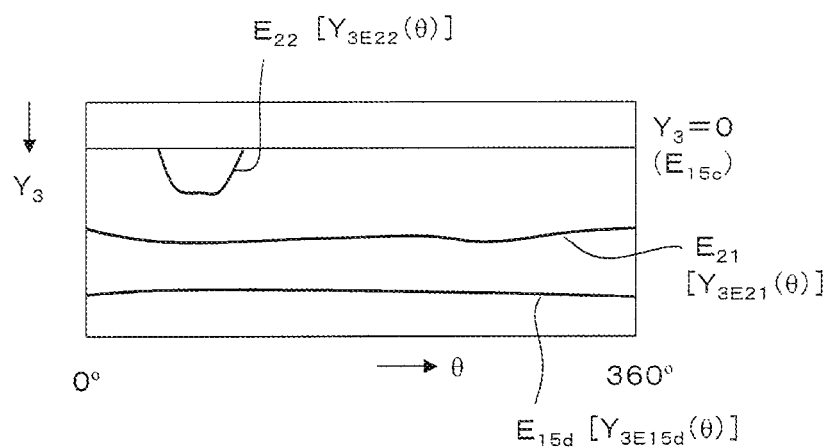
FIG. 18B A view showing corrected positions $Y_5$ on an image correcting the positions Y at FIG. 18A with reference to boundary line positions $Y_{E15c(\theta)}$ corresponding to the third boundary edge 15c.

The third captured image data $DI_{Lb}$ is corrected so that longitudinal direction positions $Y_3(\theta)$ at corresponding positions (θ) along the circumferential direction of the different pixel points on the third captured image are expressed with reference to longitudinal direction positions $Y_{E15c}(\theta)$ at different positions (θ) along the circumferential direction of the boundary line $E_{15c}$ between the lower outer circumference bevel surface image part $I_{12L}$ on the corresponding third captured image and its outer image part $I_{BKU}$. Specifically, as shown in FIG. 18B, the longitudinal direction positions $Y_3(\theta)$ at the different positions (θ) along the circumferential direction of the boundary line $E_{15c}$ are made zero ($Y_3=0$), and the longitudinal direction positions $Y_3(\theta)$ at the corresponding positions (θ) along the circumferential direction of the different pixel points are expressed as distances from the boundary line $E_{15c}$. That is, post-correction longitudinal direction positions $Y_3(\theta)$ at the different positions (θ) along the circumferential direction of the different pixel points on the third captured image are similarly expressed by the pre-correction longitudinal direction positions $Y_{E15c}(\theta)$ at corresponding positions (θ) along the circumferential direction of the boundary line $E_{15c}$ and the pre-correction longitudinal direction positions $Y(\theta)$ at corresponding positions (θ) along the circumferential direction of corresponding pixel points as $$Y_3(\theta)=Y(\theta)-Y_{E15c}(\theta)$$

Due to such correction of the third captured image data $DI_{Lb}$, as shown in FIG. 18B, the post-correction longitudinal direction positions $Y_{3E15c}(\theta)$ at different positions (θ) along the circumferential direction of the boundary line $E_{15cd}$ of the other side of the lower outer circumference bevel surface image $I_{12L}$ on the third captured image are similarly expressed using the pre-correction longitudinal direction positions $Y_{E15dL}(\theta)$ at corresponding positions (θ) along the circumferential direction of the same boundary line $E_{15d}$ as $$Y_{3E15d}(\theta)=Y_{E15dL}(\theta)-Y_{E15c}(\theta)$$

Further, the post-correction longitudinal direction positions $Y_{3E22}(\theta)$ at different positions (θ) along the circumferential direction of the edge line $E_{22}$ of the second film layer image part $I_{12L}$ (22) corresponding to the second film layer 22 on the third captured image (film layer edge position information) are similarly expressed using the pre-correction longitudinal direction positions $Y_{E22}(\theta)$ at corresponding positions (θ) along the circumferential direction of the same edge line $E_{22}$ as $$Y_{3E22}(\theta)=Y_{E22}(\theta)-Y_{E15c}(\theta)$$

Further, the longitudinal direction positions $Y_{2E21}(\theta)$ at different positions (θ) along the circumferential direction of the edge line $E_{21}$ of the first film layer image part $I_{12L}$ (21) corresponding to the first film layer 21 (film layer edge position information) are similarly expressed using the pre-correction longitudinal direction positions $Y_{E21}(\theta)$ at corresponding positions (θ) along the circumferential direction of the same edge line $E_{21}$ as $$Y_{3E21}(\theta)=Y_{E21}(\theta)-Y_{E15c}(\theta)$$

Figure 15B:
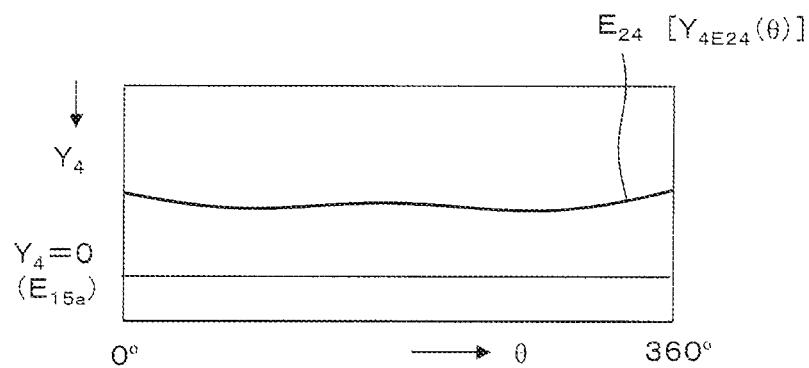

Further, the fourth captured image data $DI_{Sa}$ is corrected so that longitudinal direction positions $Y_4(\theta)$ at corresponding positions (θ) along the circumferential direction of the different pixel points on the fourth captured image are expressed with reference to longitudinal direction positions $Y_{E15aL}(\theta)$ at different positions (θ) along the circumferential direction of the boundary line $E_{15a}$ between the upper surface image part $I_{Sa}$ on the corresponding fourth captured image and its outer image part $I_{BKL}$. Specifically, as shown in FIG. 15B, the longitudinal direction positions $Y_4(\theta)$ at the different positions (θ) along the circumferential direction of the boundary line $E_{15b}$ are made zero ($Y_4=0$), and the longitudinal direction positions $Y_4(\theta)$ at the corresponding positions (θ) along the circumferential direction of the different pixel points are expressed as distances from the boundary line $E_{15a}$. That is, post-correction longitudinal direction positions $Y_4(\theta)$ at the different positions (θ) along the circumferential direction of the different pixel points on the fourth captured image are similarly expressed by the pre-correction longitudinal direction positions $Y_{E15aL}(\theta)$ at corresponding positions (θ) along the circumferential direction of the boundary line $E_{15a}$ and the pre-correction longitudinal direction positions $Y(\theta)$ at corresponding positions (θ) along the circumferential direction of corresponding pixel points as $$Y_4(\theta)=Y(\theta)-Y_{E15aL}(\theta)$$

Due to such correction of the fourth captured image data $DI_{Sa}$, the post-correction longitudinal direction positions $Y_{4E24}(\theta)$ at different positions (θ) along the circumferential direction of the edge line $E_{24}$ of the fourth film layer image part $I_{Sb}$(24) corresponding to the fourth film layer 24 on the fourth captured image are similarly expressed using the pre-correction longitudinal direction positions $Y_{E24}(\theta)$ at corresponding positions (θ) along the circumferential direction of the same edge line $E_{24}$ as $$Y_{4E24}(\theta)=Y_{E24}(\theta)-Y_{E15aL}(\theta)$$

Figure 19B:
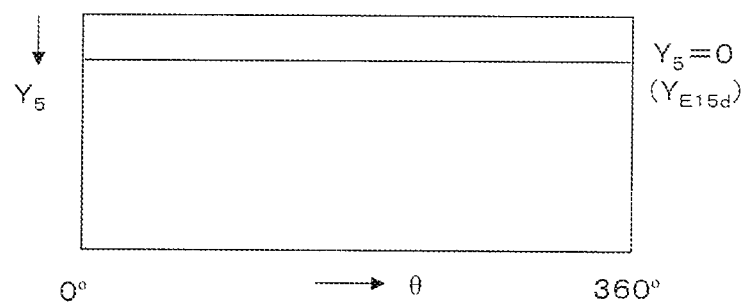
FIG. 19B A view showing corrected positions $Y_5$ on an image correcting the positions Y at FIG. 19A with reference to boundary line positions $Y_{E15d(\theta)}$ corresponding to the fourth boundary edge 15d.

Furthermore, the fifth captured image data $DI_{Sb}$ is corrected so that longitudinal direction positions $Y_5(\theta)$ at corresponding positions (θ) along the circumferential direction of the different pixel points on the fifth captured image are expressed with reference to longitudinal direction positions $Y_{E15d}(\theta)$ at different positions ($\theta$) along the circumferential direction of the boundary line $E_{15d}$ between the bottom surface image part $I_{Sb}$ on the corresponding fifth captured image and its outer image part $I_{BKU}$. Specifically, as shown in FIG. 19B, the longitudinal direction positions $Y_5(\theta)$ at the different positions ($\theta$) along the circumferential direction of the boundary line $E_{15d}$ are made zero ($Y_5=0$), and the longitudinal direction positions $Y_5(\theta)$ at the corresponding positions ($\theta$) along the circumferential direction of the different pixel points are expressed as distances from the boundary line $E_{15d}$. That is, post-correction longitudinal direction positions $Y_5(\theta)$ at the different positions ($\theta$) along the circumferential direction of the different pixel points on the fifth captured image are similarly expressed by the pre-correction longitudinal direction positions $Y_{E15d}(\theta)$ at corresponding positions ($\theta$) along the circumferential direction of the boundary line $E_{15d}$ and the pre-correction longitudinal direction positions $Y(\theta)$ at corresponding positions ($\theta$) along the circumferential direction of corresponding pixel points as $$Y_5(\theta)=Y(\theta)-Y_{E15d}(\theta)$$

When the above-mentioned correction processing of the captured image data $DI_{Ub}$, $DI_{Ap}$, $DI_{Lb}$, and $DI_{Sb}$ (S16) ends, the processing unit 200 shifts to the processing shown in FIG. 10 and generates a composite image (composite image data) from the corrected captured image data $DI_{Ub}$, $DI_{Ap}$, $DI_{Lb}$, $DI_{Sa}$, and $DI_{Sb}$ (S17). This composite image is generated as follows: Note that, in the processing for generating this composite image, for example, the boundary line $E_{15a}$ between the upper surface outer circumference bevel surface image part $I_{12U}$ and outer image part $I_{BKU}$ included in the first captured image expressed by the first captured image data $DI_{Ub}$ is determined as the reference boundary line.

The upper outer circumference bevel surface image part $I_{12U}$ and the upper surface image part $I_{Sa}$ are combined so that the boundary line $E_{15a}$ between the upper outer circumference bevel surface image part $I_{12U}$ and outer image part $I_{BKU}$ serving as the reference for correction in the first captured image (see FIG. 16A and FIG. 16B) and the boundary line $E_{15a}$ between the upper surface image part $I_{Sa}$ and outer part $I_{BKL}$ serving as the reference for correction in the fourth captured image (see FIG. 15A and FIG. 15B) match. Further, the upper outer circumference bevel surface image part $I_{12U}$ and outer circumference end face image part $I_{12A}$ are combined so that the boundary line $E_{15b}$ between the upper outer circumference bevel surface image part $I_{12U}$ and outer image part $I_{BKL}$ (see FIG. 16A and FIG. 16B) and the boundary line $E_{15b}$ between the outer circumference end face image part $I_{12A}$ and outer image part $I_{BKU}$ serving as the reference for correction in the second captured image (see FIG. 17A and FIG. 17B) match. The outer circumference end face image part $I_{12A}$ and lower outer circumference bevel surface image part $I_{12L}$ are combined so that the boundary line $E_{15c}$ between the outer circumference end face image part $I_{12A}$ and outer image part $I_{BKL}$ (see FIG. 17A and FIG. 17B) and the boundary line $E_{15c}$ between the lower outer circumference bevel surface image $I_{12L}$ and outer image part $I_{BKU}$ serving as the reference for correction in the third captured image (see FIG. 18A and FIG. 18B) match. Furthermore, the lower outer circumference bevel surface image part $I_{12L}$ and bottom surface image part $I_{Sb}$ are combined so that the boundary line $E_{15d}$ between the lower outer circumference bevel surface image $I_{12L}$ and outer image part $I_{BKL}$ (see FIG. 18) and the boundary line $E_{15d}$ between the bottom surface image part $I_{Sb}$ and outer image part $I_{BKU}$ serving the reference for correction in the fifth captured image (see FIG. 19A and FIG. 19B) match.

Figure 20:
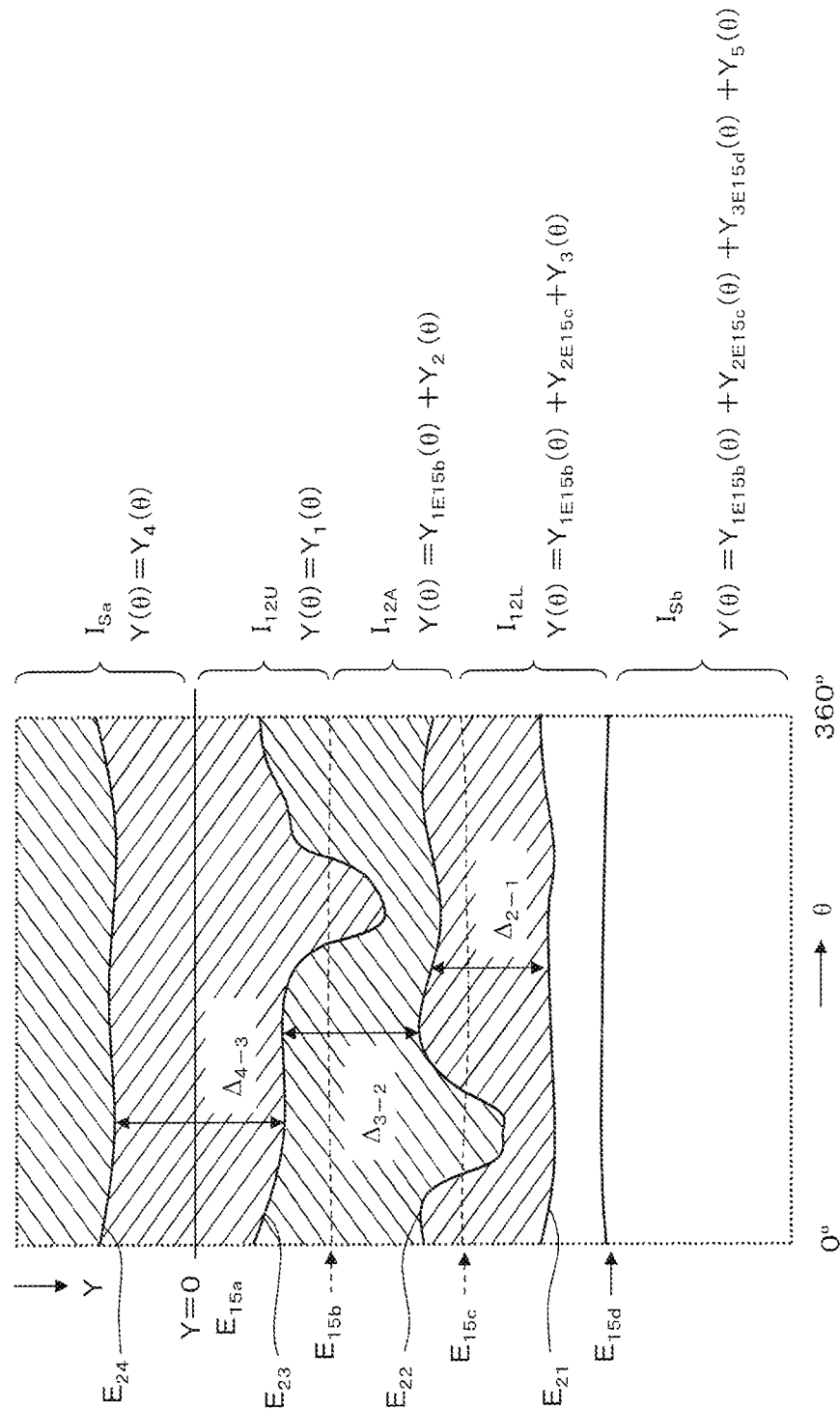
FIG. 20 A view showing a composite image obtained by combining five images obtained from five camera units of a first camera unit to fifth camera unit.

In this way, a composite image such as shown in FIG. 20 comprised of parts contained in the different captured images such as the upper surface image part $I_{Sa}$, upper outer circumference bevel surface image part $I_{12U}$, outer circumference end face image part $I_{12A}$, lower outer circumference bevel surface image part $I_{12L}$, and bottom surface image part $I_{Sb}$ combined is generated. In this composite image, the longitudinal direction positions $Y(\theta)$ at the different positions ($\theta$) along the circumferential direction of the different pixel points are determined with reference to the longitudinal direction positions at the corresponding positions along the circumferential direction of the boundary line $E_{15a}$ of the first captured image forming the reference boundary line.

Therefore, as shown in FIG. 20, in the region of the upper surface image part $I_{Sa}$ of the composite image, the values of the longitudinal direction positions $Y(\theta)$ at the different positions ($\theta$) along the circumferential direction of the different pixel points are determined so as to correspond to the values of the longitudinal direction positions $Y_4(\theta)$ at the corresponding positions ($\theta$) along the circumferential direction of the different pixel points obtained by correction with reference to the boundary line $E_{15a}$ from the fourth captured image data $DI_{Sa}$ as explained above (see FIG. 15B). For example, this becomes $$Y(\theta)=Y_4(\theta)$$

In the region of the upper outer circumference bevel surface image part $I_{12U}$ of the composite image, the values of the longitudinal direction positions $Y(\theta)$ at the different positions ($\theta$) along the circumferential direction of the different pixel points are determined so as to correspond to the values of the longitudinal direction positions $Y_1(\theta)$ at the corresponding positions ($\theta$) along the circumferential direction of the different pixel points obtained by correction with reference to the boundary line $E_{15a}$ from the first captured image data $DI_{Ub}$ as explained above (see FIG. 16B). For example, this becomes $$Y(\theta)=Y_1(\theta)$$

Further, in the region of the outer circumference end face image part $I_{12A}$ of the composite image, the values of the longitudinal direction positions $Y(\theta)$ at the different positions ($\theta$) along the circumferential direction of the different pixel points are determined so as to correspond to the values of the longitudinal direction positions $Y_2(\theta)$ at the corresponding positions ($\theta$) along the circumferential direction of the different pixel points obtained by correction with reference to the boundary line $E_{15b}$ from the second captured image data $DI_{Ap}$ as explained above (see FIG. 17B) plus the distances ($Y_{1E15b}(\theta)$) from the reference boundary line $E_{15a}$ at the corresponding positions ($\theta$) along the circumferential direction of the boundary line $E_{15b}$. For example, this becomes $$Y(\theta)=Y_{1E15b}(\theta)+Y_2(\theta)$$

Furthermore, in the region of the lower outer circumference bevel surface image part $I_{12L}$ of the composite image, the values of the longitudinal direction positions $Y(\theta)$ at the different positions ($\theta$) along the circumferential direction of the different pixel points are determined so as to correspond to the values of the longitudinal direction positions $Y_3(\theta)$ at the corresponding positions ($\theta$) along the circumferential direction of the different pixel points obtained by correction with reference to the boundary line $E_{15c}$ from the third captured image data $DI_{Lb}$ as explained above (see FIG. 18B) plus the distances ($Y_{1E15b}(\theta)+Y_{2E15c}(\theta)$) from the reference boundary line $E_{15a}$ at the corresponding positions (θ) along the circumferential direction of the boundary line $E_{15c}$. For example, this becomes $$Y(\theta)=Y_{1E15b}(\theta)+Y_{2E15c}(\theta)+Y_3(\theta)$$

Further, in the region of the bottom surface image part $I_{Sb}$ of the composite image, the values of the longitudinal direction positions Y (θ) at the different positions (θ) along the circumferential direction of the different pixel points are determined so as to correspond to the values of the longitudinal direction positions $Y_5$ (θ) at the corresponding positions (θ) along the circumferential direction of the different pixel points obtained by correction with reference to the boundary line $E_{15d}$ from the fifth captured image data $DI_{Sb}$ as explained above (see FIG. 19B) plus the distances $(Y_{1E15b}(\theta)+Y_{2E15c}(\theta)+Y_{3E15d}(\theta))$ from the reference boundary line $E_{15a}$ at the corresponding positions (θ) along the circumferential direction of the boundary line $E_{15d}$. For example, this becomes $$Y(\theta)=Y_{1E15b}(\theta)+Y_{2E15c}(\theta)+Y_{3E15d}(\theta)+Y_5(\theta)$$

When a composite image (composite image data) is generated in the above-mentioned way, the processing unit 200 can use this composite image data to display on the display unit 220 a composite image such as shown in FIG. 20. Further, returning to FIG. 10, the processing unit 200 detects the edge lines $E_{21}$, $E_{22}$, $E_{23}$, and $E_{24}$ of the film layer image parts corresponding to the film layers 21, 22, 23, and 24 on the composite image by a usual edge detection technique (S18). The longitudinal direction positions $Y_{E21}$ (θ), $Y_{E22}$ (θ), $Y_{E23}$ (θ), and $Y_{E24}$ (θ) at the different positions (θ) along the circumferential direction of the different edge lines $E_{21}$, $E_{22}$, $E_{23}$, and $E_{24}$ (film layer edge position information) can be expressed by a predetermined coordinate system Y-θ on the composite image. However, the longitudinal direction positions $Y_{E21}$ (θ), $Y_{E22}$ (θ), $Y_{E23}$ (θ), and $Y_{E24}$ (θ) at the different positions (θ) along the circumferential direction of the edge lines, as explained above, maintain a relative relationship with reference to longitudinal direction positions at corresponding positions (θ) along the circumferential direction of the boundary line $E_{15a}$ on the first captured image.

Furthermore, the processing unit 200 measures the distances between edge lines of the film layer images on the composite image obtained in the above-mentioned way (S19). For example, as shown in FIG. 20, the distance $\Delta_{4-3}$ (θ) $(=Y_{E24}(\theta)-Y_{E23}(\theta))$ between the edge line $E_{23}$ of the film layer image part corresponding to the film layer 23 and the edge line $E_{24}$ of the film layer image part corresponding to the film layer 24 laid over this film layer 23, the distance $\Delta_{3-2}$ (θ) $(=Y_{E23}(\theta)-Y_{E22}(\theta))$ between the edge line $E_{22}$ of the film layer image part corresponding to the film layer 22 and the edge line $E_{23}$ of the film layer image part corresponding to the film layer 23 laid over this film layer 22, and the distance $\Delta_{2-1}$ (θ) $(=Y_{E22}(\theta)-Y_{E21}(\theta))$ between the edge line $E_{21}$ of the film layer image part corresponding to the film layer 21 and the edge line $E_{22}$ of the film layer image part corresponding to the film layer 22 laid over this film layer 21 are measured on the composite image.

Further, the processing unit 200 can use the longitudinal direction positions $Y_{E21}$ (θ), $Y_{E22}$ (θ), $Y_{E23}$ (θ), and $Y_{E24}$ (θ) of different positions (θ) along the circumferential direction of the edge lines $E_{21}$, $E_{22}$, $E_{23}$, and $E_{24}$ of the film layer image parts (film layer edge position information) and the distances between edge lines $\Delta A_{4-3(\theta)}$ $(=Y_{E24}(\theta)-Y_{E23}(\theta))$, $\Delta_{3-2(\theta)}$ $(=Y_{E23}(\theta)-Y_{E22}(\theta))$, and $\Delta_{2-1}(\theta)$ $(=Y_{E22}(\theta)-Y_{E21}(\theta))$ to generate evaluation information of the film layers 21 to 24 formed on the surface of the wafer 10 under inspection (S20). This evaluation information may be the longitudinal direction positions $Y_{E21}$ (θ), $Y_{E22}$ (θ), $Y_{E23}$ (θ), and $Y_{E24}$ (θ) of different positions (θ) along the circumferential direction of the edge lines $E_{21}$, $E_{22}$, $E_{23}$, and $E_{24}$ of the film layer image parts (film layer edge position information) and the distances between edge lines $\Delta_{4-3(\theta)}$ $(=Y_{E24}(\theta)-Y_{E23}(\theta))$, $\Delta_{3-2(\theta)}(=Y_{E23}(\theta)-Y_{E22}(\theta))$, and $\Delta_{2-1}(\theta)$ $(=Y_{E22}(\theta)-Y_{E21}(\theta))$ themselves expressed by a predetermined format, for example, may be rank information obtained by threshold processing or quality judgment information. Further, it is also possible to use information obtained by statistically processing evaluation information of a plurality of wafers 10 as the evaluation information.

The processing unit 200 makes the display unit 220 display the above-mentioned composite image and the obtained evaluation information (output processing: S21), then ends the processing. The operator can use the composite image and various evaluation information displayed on the display unit 220 to judge the quality of a wafer 10 under inspection or the suitability of conditions in the process for forming film layers on the surface of a wafer 10.

According to the above-explained inspection apparatus, longitudinal direction positions at different positions along the circumferential direction of a boundary line $E_{15a}$ on a captured image corresponding to the boundary between the upper surface 11*a* and upper outer circumference bevel surface 12U, constituting the first boundary edge 15*a*, are used as a reference to determine longitudinal direction positions at corresponding positions along the circumferential direction of edge lines of film layer image parts on the composite image. This is obtained as film layer edge position information. It is possible to use that film layer edge position information to evaluate the edge positions of the different film layers with reference to the boundary between the upper surface 11*a* and upper outer circumference bevel surface 12U constituting the first boundary edge 15*a*. Therefore, it becomes possible to precisely quantitatively evaluate the positions of edge lines of film layers on the wafer 10.

Further, according to the above-mentioned inspection apparatus, captured image data expressing captured images corresponding to fields of view including surfaces of the wafer 10 such as the upper surface outer circumference part, upper outer circumference bevel surface 12U, outer circumference end face 12A, lower outer circumference bevel surface 12L, and lower surface outer circumference part is used to generate composite image data expressing a composite image (see FIG. 20) of a plurality of surface image parts corresponding to these surfaces combined with corresponding boundary lines matched, and the composite image data is used to display a composite image on the display unit 220, so it is possible to use the composite image displayed on the display unit 220 to obtain a comprehensive grasp of the states of the contiguous surfaces of the wafer 10 such as the upper surface outer circumference part, upper outer circumference bevel surface 12U, outer circumference end face 12A, lower outer circumference bevel surface 12L, and lower surface outer circumference part. Specifically, using film layer edge position information expressing edge lines of film layer image parts corresponding to film layers on this composite image, no matter which of the surfaces of the wafer 10 among the upper surface 11*a*, upper outer circumference bevel surface 12U, outer circumference end face 12A, lower outer circumference bevel surface 12L, and lower surface 11*b* the film layers are formed on, it is possible to express positions of edge lines by a uniform reference and possible to precisely and quantitatively evaluate (inspect) positions of formation of the film layers formed on the surface of the wafer 10. Furthermore, specifically, as shown in FIG. 20, even distances between edge lines of two film layers formed on different surfaces can be quantitatively evaluated by the distances $\Delta_{4\text{-}3}$, $\Delta_{3\text{-}2}$, and $\Delta_{2\text{-}1}$ between edge lines of the corresponding two film layer image parts.

Note that, the plurality of surfaces for which images are captured need not be the above-mentioned five surfaces. They may also be two contiguous surfaces among the upper surface outer circumference part, upper outer circumference bevel surface 12U, outer circumference end face 12A, lower outer circumference bevel surface 12L, and lower surface outer circumference part. In particular, when desiring to evaluate the state of entry of film layers to the upper outer circumference bevel surface 12U, outer circumference end face 12A, and lower outer circumference bevel surface 12L of the wafer 10, it is possible to capture images of only these surfaces (for inspection) and generate a composite image from the images obtained from these surfaces.

Further, it is also possible to evaluate the edge lines of film layers by a single captured image without combining the first captured image to fifth captured image corresponding to the upper outer circumference part, upper outer circumference bevel surface 12U, outer circumference end face 12A, lower outer circumference bevel surface 12L, and lower surface outer circumference part. In this case, the longitudinal direction positions at the different positions along the circumferential direction of the boundary lines ($E_{15a}$, $E_{15c}$, and $E_{15d}$) between the surface image parts, corresponding to surfaces on captured images corresponding to fields of view including any surfaces of the wafer 10 of the upper outer circumference part, upper outer circumference bevel surface 12U, outer circumference end face 12A, lower outer circumference bevel surface 12L, and lower surface outer circumference part, and their outer image parts are used as reference to generate film layer edge position information expressing longitudinal direction positions at corresponding positions along the circumferential direction of edge lines of film layer image parts. Even if the widths or angles of inclination of the different surfaces fluctuate in various ways, the film layer edge position information may be used to precisely quantitatively evaluate the positions of edge lines of the film layers as distances from boundary edges between those surfaces and the surfaces adjoining them.

In the above-mentioned example, a composite image was displayed, but individual captured images (FIG. 14B, FIG. 15B, FIG. 16B, FIG. 17B, FIG. 18B, and FIG. 19B) may also be displayed. Further, it is also possible to use positions corrected by correction processing (see FIG. 9: S16) to express edge lines or boundary lines of film layer image parts and display those edge lines or boundary lines superposed over the pre-correction captured images (for example, display FIG. 15A and FIG. 15B superposed).

INDUSTRIAL APPLICABILITY

As explained above, the inspection apparatus of a disk-shaped substrate according to the present invention is designed to be able to quantitatively inspect positions of formation of film layers formed on a surface of a disk-shaped substrate. Further, since it is designed to be able to quantitatively inspect positions of formation of film layers formed on a surface of a disk-shaped substrate, it is useful as an inspection apparatus of a disk-shaped substrate for capturing an image of and inspecting an outer circumference part of a semiconductor wafer or other disk-shaped substrate.

The invention claimed is:

1. An inspection apparatus of a disk-shaped substrate having film layers formed on its surface, which has an image capturing unit having a capturing view field including a predetermined surface at an outer circumference part of said disk-shaped substrate, successively capturing images of said predetermined surface in a circumferential direction of said disk-shaped substrate, and outputting image signals and an image processor processing the image signals successively output from said image capturing unit;

said image processor having an image data generating means for generating captured image data expressing a captured image corresponding to said capturing view field extending corresponding to the circumferential direction of said disk-shaped substrate based on said image signals and a film layer edge position information generating means for generating film layer edge position information from said captured image data using as a reference longitudinal direction positions showing positions in a direction traversing said circumferential direction at respective positions along said circumferential direction of a boundary line between a surface image part corresponding to said predetermined surface on said captured image and its outer image part, said film layer edge position information expressing longitudinal direction positions at corresponding positions along said circumferential direction of edge lines of film layer image parts corresponding to said film layers on said surface image part, wherein said film layer edge position information generating means has a means for detecting the longitudinal direction positions at respective positions along said circumferential direction of a boundary line between said surface image part on said captured image and said outer image part, a means for detecting the longitudinal direction positions at respective positions along said circumferential direction of the edge line of said film layer image part on said surface image part, and a correcting means for correcting the detected longitudinal direction positions at the respective positions along said circumferential direction of the edge line of said film layer image part using as the reference the longitudinal direction positions at the corresponding positions along said circumferential direction of the boundary line between said surface image part and said outer image part, and generating said film layer edge position information, and wherein said film layer edge position information is used to evaluate positions of formation of said film layers at said disk-shaped substrate.

2. An inspection apparatus of a disk-shaped substrate as set forth in claim 1, wherein said disk-shaped substrate is a semiconductor wafer formed with an upper outer circumference bevel surface inclined from an edge of an upper surface toward a lower surface, a lower outer circumference bevel surface inclined from an edge of said lower surface toward said upper surface, and an outer circumference end face connecting said upper outer circumference bevel surface and said lower outer circumference bevel surface at an outer circumference part of said semiconductor wafer, and said image capturing unit captures an image of at least one of a region of said upper surface adjoining said upper outer circumference bevel surface, said upper outer circumference bevel surface, said outer circumference end face, said lower outer circumference bevel surface, and a region of said lower surface adjoining said lower outer circumference bevel surface.

3. An inspection apparatus of a disk-shaped substrate as set forth in claim 2, wherein said image capturing unit captures an image of the region of said upper surface of said semiconductor wafer adjoining said upper outer circumference bevel surface, said image data generating means uses the image signals successively output from said image capturing unit as a basis to generate captured image data expressing a captured image corresponding to a field of view including the region of said upper surface adjoining said upper outer circumference bevel surface extending along the circumferential direction of said semiconductor wafer, and said film layer edge position information generating means generates film layer edge position information from said captured image data using as a reference longitudinal direction positions at positions along said circumferential direction of a boundary line between an upper surface image part corresponding to the region of said upper surface adjoining said upper outer circumference bevel surface on said captured image and an outer image part at the upper outer circumference bevel surface side, said film layer edge position information expressing longitudinal direction positions at corresponding positions along said circumferential direction of an edge line of a film layer image part corresponding to said film layer at said upper surface image part.

4. An inspection apparatus of a disk-shaped substrate as set forth in claim 2, wherein said image capturing unit captures an image of said upper outer circumference bevel surface of said semiconductor wafer, said image data generating means uses the image signals successively output from said image capturing unit as a basis to generate captured image data expressing a captured image corresponding to a field of view including, said upper outer circumference bevel surface extending corresponding to the circumferential direction of said semiconductor wafer, and said film layer edge position information generating means generates film layer edge position information from said captured image data using as a reference longitudinal direction positions at respective positions along said circumferential direction of a boundary line between an upper outer circumference bevel surface image part corresponding to said upper outer circumference bevel surface on said captured image and either an outer image part at the upper surface side or an outer image part at the outer circumference end face side, said film layer edge position information expressing longitudinal directional positions at corresponding positions along said circumferential direction of an edge line of a film layer image part corresponding to said film layer at said upper outer circumference bevel surface image part.

5. An inspection apparatus of a disk-shaped substrate as set forth in claim 2, wherein said image capturing unit captures an image of said outer circumference end face of said semiconductor wafer, said image data generating means uses the image signals successively output from said image capturing unit as a basis to generate captured image data expressing a captured image corresponding to a field of view including said outer circumference end face extending corresponding to the circumferential direction of said semiconductor wafer, and said film layer edge position information generating means generates film layer edge position information from said captured image data using as a reference longitudinal direction positions at respective positions along said circumferential direction of a boundary line between an outer circumference bevel end face image part corresponding to said outer circumference end face on said captured image and either an outer image part at the upper outer circumference bevel surface side or an outer image part at the lower outer circumference bevel surface side, said film layer edge position information expressing longitudinal directional positions at corresponding positions along said circumferential direction of an edge line of a film layer image part corresponding to said film layer at said upper outer circumference end face image part.

6. An inspection apparatus of a disk-shaped substrate as set forth in claim 2, wherein said image capturing unit captures an image of said lower outer circumference bevel surface of said semiconductor wafer, said image data generating means uses the image signals successively output from said image capturing unit as a basis to generate captured image data expressing a captured image corresponding to a field of view including said lower outer circumference bevel surface extending corresponding to the circumferential direction of said semiconductor wafer, and said film layer edge position information generating means generates film layer edge position information from said captured image data using as a reference longitudinal direction positions at respective positions along said circumferential direction of a boundary line between a lower outer circumference bevel surface image part corresponding, to said lower outer circumference bevel surface on said captured image and either of an outer image part at the outer circumference end face side and an, outer image part at the lower surface side, said film layer edge position information expressing longitudinal direction positions at corresponding positions along said circumferential direction of an edge line of the film layer part corresponding to said film layer on said lower outer circumference bevel surface image.

7. An inspection apparatus of a disk-shaped substrate as set forth in claim 2, wherein said image capturing unit captures an image of a region of said lower surface of said semiconductor wafer adjoining said lower outer circumference bevel surface, said image data generating means uses the image signals successively output from said image capturing unit as a basis to generate captured image data expressing a captured image corresponding to a field of view including the region of said lower surface of said semiconductor wafer adjoining said lower outer circumference bevel surface extending corresponding to the circumferential direction, and said film layer edge position information generating means generates film layer edge position information from said captured image data using as a reference longitudinal direction positions at respective positions along said circumferential direction of a boundary line between a bottom surface image part corresponding to a region of said lower surface on said captured image adjoining said lower outer circumference bevel surface and an outer image part at the lower outer circumference bevel surface side, said film layer edge position information expressing longitudinal direction positions at corresponding positions along said circumferential direction of an edge line of a film layer image part corresponding to said film layer at said bottom surface image part.

8. An inspection apparatus of a disk-shaped substrate having film layers formed on its surface, which has an image capturing unit having individual capturing view fields each of which includes one of a plurality of surfaces continuous along a direction traversing a circumferential direction at an outer circumference part of said disk-shaped substrate, successively capturing images of said plurality of surfaces in the circumferential direction of said disk-shaped substrate, and outputting image signals and an image processor processing the image signals successively output from said image capturing unit;

said image processor having an image data generating means for generating captured image data expressing a captured image corresponding to each of said capturing view fields respectively including said plurality of surfaces extending corresponding to the circumferential direction of said disk-shaped substrate based on said image signals, a correcting means for correcting said captured image data expressing the captured image so that longitudinal direction positions at respective positions along said circumferential direction of respective pixel points on said captured image are expressed using as a reference longitudinal direction positions at the respective positions along said circumferential direction of a boundary line between a surface image part corresponding to the surface on said captured image corresponding to each of the capturing view fields respectively including said plurality of surfaces and an outer image part at one side adjoining said surface, the longitudinal direction positions showing positions in a direction traversing said circumferential direction, an image combining means for using said corrected captured image data corresponding to each of the capturing view fields respectively including said plurality of surfaces, and generating image data expressing a composite image in which a plurality of surface image pans corresponding to said plurality of surfaces are combined so that their corresponding boundary lines are matched, and in which longitudinal direction positions at respective positions along said circumferential direction of the respective pixel points on said composite image are determined using as a reference longitudinal direction positions at the respective positions along said circumferential direction of a reference boundary line, a boundary line on the captured image corresponding to a capturing view field including a predetermined surface of said plurality of surfaces being used as the reference boundary line, and a film layer edge position information generating means for generating film layer edge position information showing longitudinal direction positions at respective positions along said circumferential direction of edge lines of film layer image parts corresponding to said film layers on said composite image, wherein said film layer edge position information is used to evaluate positions of formation of said film layers at said disk-shaped substrate.

9. An inspection apparatus of a disk-shaped substrate as set forth in claim 8, wherein said disk-shaped substrate is a semiconductor wafer on which an upper outer circumference bevel surface inclined from an edge of an upper surface toward a lower surface, an outer circumference end face contiguous from an edge of said upper outer circumference bevel surface, and a lower outer circumference bevel surface inclined from an edge of the lower surface toward said upper surface and contiguous from said outer circumference end face are formed contiguously in a direction traversing said circumferential direction, and said plurality of surfaces are two or more contiguous surfaces among a region of said upper surface adjoining said upper outer circumference bevel surface, said upper outer circumference bevel surface, said outer circumference end face, said lower outer circumference bevel surface, and a region of the lower surface adjoining said lower outer circumference bevel surface.

10. An inspection apparatus of a disk-shaped substrate as set forth in claim 9, wherein said plurality of surfaces are said upper outer circumference bevel surface, said outer circumference end face, and said lower outer circumference bevel surface;

said image data generating means generates, based on the image signals successively output, from said image capturing unit, first captured image data expressing a first captured image corresponding to a field of view including said upper outer circumference bevel surface, second captured image data expressing a second captured image corresponding to a field of view including said outer circumference end face, and third captured image data expressing a third captured image corresponding to a field of view including said lower outer circumference bevel surface;

said correcting means corrects said first captured image data so that longitudinal direction positions at respective positions along said circumferential direction of respective pixel points on said first captured image are expressed using as a reference longitudinal direction positions at the respective positions along said circumferential direction of a boundary line between an upper outer circumference bevel surface image part corresponding to said upper outer circumference bevel surface on said first captured image and an outer image part at an upper surface side of the same, corrects said second captured image data so that longitudinal direction positions at respective positions along said circumferential direction of respective pixel points on said second captured image are expressed using as a reference to longitudinal direction positions at the respective positions along said circumferential direction of a boundary line between an outer circumference end face image part corresponding to said outer circumference end face on said second captured image and an outer image part at an upper outer circumference bevel surface side of the same, and corrects said third captured image data so that longitudinal direction positions at respective positions along said circumferential direction of respective pixel points on said third captured image are expressed using as a reference longitudinal direction positions at the respective positions along said circumferential direction of a boundary line between a lower outer circumference bevel surface image part corresponding to said lower outer circumference bevel surface on said third captured image and an outer image part at the outer circumference end face side of the same; and said image combining means uses the corrected first captured image data, the corrected second captured image data, and the corrected third captured image data to generate composite image data showing a composite image of said upper outer circumference bevel surface image part, said outer circumference end face image part, and said lower outer circumference bevel surface image part combined so that their corresponding boundary lines are matched, wherein a boundary line on said first captured image is used as a reference boundary line and wherein longitudinal direction positions at respective positions along said circumferential direction of respective pixel points on said composite image are determined using as a reference longitudinal direction positions at the respective positions along said circumferential direction of said reference boundary line.

11. An inspection apparatus of a disk-shaped substrate as set forth in claim 9, wherein
said plurality of surfaces are a region of the upper surface of said semiconductor wafer adjoining said upper outer circumference bevel surface, said upper outer circumference bevel surface, said outer circumference end face, said lower outer circumference bevel surface, and a region of the lower surface of said semiconductor wafer adjoining said lower outer circumference bevel surface;
said image data generating means generates, based on the image signals successively output from said image capturing unit, first captured image data expressing a first captured image corresponding to a field of view including said upper outer circumference bevel, second captured image data expressing a second captured image corresponding to a field of view including said outer circumference end face, third captured image data expressing a third captured image corresponding to a field of view including said lower outer circumference bevel surface, fourth captured image data expressing a fourth captured image corresponding to a field of view including the region of said upper surface adjoining the upper outer circumference bevel surface, and fifth captured image data expressing a fifth captured image corresponding to a field of view including the region of said lower surface adjoining said lower outer circumference bevel surface;
said correcting means
corrects said first captured image data so that longitudinal direction positions at respective positions along said circumferential direction of respective pixel points on said first captured image are expressed using as a reference longitudinal direction positions at the respective positions along said circumferential direction of a boundary line between an upper outer circumference bevel surface image part corresponding to said upper outer circumference bevel surface on said first captured image and an outer image part at an upper surface side of the same,
corrects said second captured image data so that longitudinal direction positions at respective positions along said circumferential direction of respective pixel points on said second captured image are expressed using as a reference longitudinal direction positions at the respective positions along said circumferential direction of a boundary line between an outer circumference end face image part corresponding to said outer circumference end face on said second captured image and an outer image part at an upper outer circumference bevel surface side of the same,
corrects said third captured image data so that longitudinal direction positions at respective positions along said circumferential direction of respective pixel points on said third captured image are expressed using as a reference longitudinal direction positions at the respective positions along said circumferential direction of a boundary line between a lower outer circumference bevel surface image part corresponding to said lower outer circumference bevel surface on said third captured image and an outer image part at the outer circumference end face side of the same,
corrects said fourth captured image data so that longitudinal direction positions at respective positions along said circumferential direction of respective pixel points on said fourth captured image are expressed using as a reference to longitudinal direction positions at the respective positions along said circumferential direction of a boundary line between an upper surface image part corresponding to the region of said upper surface on said fourth captured image adjoining said upper outer circumference bevel surface and an outer image part at an upper outer circumference bevel surface side of the same, and
corrects said fifth captured image data so that longitudinal direction positions at respective positions along said circumferential direction of respective pixel points on said fifth captured image are expressed using as a reference longitudinal direction positions at the respective positions along said circumferential direction of a boundary line between a bottom surface image part corresponding to the region of said lower surface on said fifth captured image adjoining, said lower outer circumference bevel surface and the outer image part at the lower outer circumference bevel surface side of the same; and
said image combining means uses the corrected first captured image data, the corrected second captured image data, the corrected third captured image data, the corrected fourth captured image data, and the corrected fifth captured image data to generate composite image data showing a composite image of said upper surface image part, said upper outer circumference bevel surface image part, said outer circumference end face image part, said lower outer circumference bevel surface image part, and said bottom surface image part combined so that their corresponding boundary lines are matched, wherein a boundary line on said first captured image is used as a reference boundary line and wherein longitudinal direction positions at respective positions along said circumferential direction of the respective pixel points on said composite images are determined using as a reference longitudinal direction positions at the respective positions along said circumferential direction of said reference boundary line.

12. An inspection apparatus of a disk-shaped substrate having
an image capturing unit having individual capturing view fields each of which includes one of a plurality of surfaces contiguous along a direction traversing a circumferential direction at an outer circumference part of said disk-shaped substrate, successively capturing images of said plurality of surfaces in the circumferential direction of said disk-shaped substrate, and outputting image signals and
an image processor processing the image signals successively output from said image capturing unit;
said image processor having
an image data generating means for generating captured image data expressing a captured image corresponding to each of said capturing view field respectively including said plurality of surfaces extending corresponding to the circumferential direction of said disk-shaped substrate based on said image signals, an image combining means for using said captured image data expressing the captured image corresponding to each of the capturing view fields respectively including said plurality of surfaces to generate composite image data expressing a composite image of the plurality of surface image parts corresponding to said plurality of surfaces combined so that their corresponding boundary lines are matched, and an output control means for displaying said composite image on a display unit based on said composite image data, wherein said image combining means has a correcting means for correcting said captured image data expressing the captured image so that longitudinal direction positions at respective positions along said circumferential direction of respective pixel points on said captured image are expressed using as a reference longitudinal direction positions at the respective positions along said circumferential direction of a boundary line between a surface image part corresponding to the surface on said captured image corresponding to each of the capturing view fields including said plurality of surfaces and the outer image part at one side adjoining said surface, the longitudinal direction positions expressing positions along in a position traversing said circumferential direction, and a composite image data generating means for using said corrected captured image data corresponding to each of the capturing view fields respectively including said plurality of surfaces, and generating image data expressing a composite image in which longitudinal direction positions at respective positions along said circumferential direction of the respective pixel points on said composite lineage are determined using as a reference longitudinal direction positions at the respective positions along said circumferential direction of a reference boundary line, a boundary line on the captured image corresponding to a capturing view field including a predetermined surface of said plurality of surfaces being used as the reference boundary line.

13. An inspection apparatus of a disk-shaped substrate as set forth in claim 12, wherein said disk-shaped substrate is a semiconductor wafer formed with an upper outer circumference bevel surface inclined from an edge of an upper surface toward a lower surface, an outer circumference end face contiguous from an edge of said upper outer circumference bevel surface, and a lower outer circumference bevel surface inclined from an edge of the lower surface toward said upper surface and contiguous from said outer circumference end face so as to be contiguous in a direction traversing said circumferential direction, and said plurality of surfaces are two or more contiguous surfaces among a region of said upper surface adjoining said upper outer circumference bevel surface, said upper outer circumference bevel surface, said outer circumference end face, said lower outer circumference bevel surface, and a region of said lower surface adjoining said lower outer circumference bevel surface.

14. An inspection apparatus of a disk-shaped substrate as set forth in claim 13, wherein said plurality of surfaces are said upper outer circumference bevel surface, said outer circumference end face, and said lower outer circumference bevel surface;

said image data generating means generates, based on the image signals successively output from said image capturing unit, first captured image data expressing a first captured image corresponding to a field of view including said upper outer circumference bevel surface, second captured image data expressing a second captured image corresponding to a field of view including said outer circumference end face, and third captured image data expressing a third captured image corresponding to a field of view including said lower outer circumference bevel surface;

said correcting means corrects said first captured image data so that longitudinal direction positions at respective positions along said circumferential direction of respective pixel points on said first captured image are expressed using as a reference longitudinal direction positions at the respective positions along said circumferential direction of a boundary line between an upper outer circumference bevel surface image part corresponding to said upper outer circumference bevel surface on said first captured image and an outer image part at an upper surface side of the same, corrects said second captured image data so that longitudinal direction positions at respective positions along said circumferential direction of respective pixel points on said second captured image are expressed using as a reference longitudinal direction positions at the respective positions along said circumferential direction of a boundary line between an outer circumference end face image part corresponding to said outer circumference end face on said second captured image and an outer image part at an upper outer circumference bevel surface side of the same, and corrects said third captured image data so that longitudinal direction positions at respective positions along said circumferential direction of respective pixel points on said third captured image are expressed using as a reference longitudinal direction positions at the respective positions along said circumferential direction of a boundary line between a lower outer circumference bevel surface image part corresponding to said lower outer circumference bevel surface on said third captured image and an outer image part at an outer circumference end face side of the same; and said composite image data generating means uses the corrected first captured image data, the corrected second captured image data, and the corrected third captured image data to generate composite image data expressing a composite image of said upper outer circumference bevel surface image part, said outer circumference end face image part, and said lower outer circumference bevel surface image part combined so that their corresponding boundary lines are matched, wherein a boundary line on said first captured image is used as a reference boundary line and wherein longitudinal direction positions at respective positions along said circumference direction of respective pixel points on said composite image are determined using as a reference longitudinal direction positions at the respective positions along said circumferential direction of said reference boundary line.

15. An inspection apparatus of a disk-shaped substrate as set forth in claim 13, wherein said plurality of surfaces are a region of the upper surface of said semiconductor wafer adjoining said upper outer circumference bevel surface, said upper outer circumference bevel surface, said outer circumference end face, said lower outer circumference bevel surface, and a region of the lower surface of said semiconductor wafer adjoining said lower outer circumference bevel surface;

said image data generating means generates, based on the image signals successively output from said image capturing unit, first captured image data expressing a first captured image corresponding to a field of view including said upper outer circumference bevel surface, second captured image data expressing a second captured image corresponding to a field of view including said outer circumference end face, third captured image data expressing a third captured image corresponding to a field of view including said lower outer circumference bevel surface, fourth captured image data expressing a fourth captured image corresponding to a field of view including the region of said upper surface adjoining the upper outer circumference bevel surface, and fifth captured image data expressing a fifth captured image corresponding to a field of view including the region of said lower surface adjoining said lower outer circumference bevel surface;

said correcting means corrects said first captured image data so that longitudinal direction positions at respective positions along said circumferential direction of respective pixel points on said first captured image are expressed using as a reference longitudinal direction positions at the respective positions along said circumferential direction of a boundary line between an upper outer circumference bevel surface image part corresponding to said upper outer circumference bevel surface on said first captured image and an outer image part at an upper surface side of the same, corrects said second captured image data so that longitudinal direction positions at respective positions along said circumferential direction of respective pixel points on said second captured image are expressed using as a reference longitudinal direction positions at the respective positions alone said circumferential direction of a boundary line between an outer circumference end face image part corresponding to said outer circumference end face on said second captured image and an outer image part at an upper outer circumference bevel surface side of the same, corrects said third captured image data so that longitudinal direction positions at respective positions along said circumferential direction of respective pixel points on said third captured image are expressed using as a reference longitudinal direction positions at the respective positions along said circumferential direction of a boundary line between a lower outer circumference bevel surface image part corresponding to said lower outer circumference bevel surface on said third captured image and an outer image part at the outer circumference end face side of the same, corrects said fourth captured image data so that longitudinal direction positions at respective positions along said circumferential direction of respective pixel points on said fourth captured image are expressed using as a reference longitudinal direction positions at the respective positions along said circumferential direction of a boundary line between an upper surface image part corresponding to the region of said upper surface on said fourth captured image adjoining said upper outer circumference bevel surface and an outer image part at an upper outer circumference bevel surface side of the same, and corrects said fifth captured image data so that longitudinal direction positions at respective positions along said circumferential direction of respective pixel points on said fifth captured image are expressed using as a reference longitudinal direction positions at the respective positions along said circumferential direction of a boundary line between a bottom surface image part corresponding to the region of said lower surface on said fifth captured image adjoining said lower outer circumference bevel surface and the outer image part at the lower outer circumference bevel surface side of the same; and said image combining means uses the corrected first captured image data, the corrected second captured image data, the corrected third captured image data, the corrected fourth captured image data, and the corrected fifth captured image data to generate composite image data showing a composite image of said upper surface image part, said upper outer circumference bevel surface image part, said outer circumference end face image part, said lower outer circumference bevel surface image part, and said bottom surface image part combined so that their corresponding boundary lines are matched, wherein a boundary line on said first captured image is used as a reference boundary line and wherein longitudinal direction positions at respective positions along said circumferential direction of the pixel points of said composite image are determined using as a reference longitudinal direction positions at the respective positions along said circumferential direction of said reference boundary line.

* * * * *